(12) United States Patent
Jacobson

(10) Patent No.: US 6,982,058 B2
(45) Date of Patent: Jan. 3, 2006

(54) METHOD FOR FABRICATING THREE DIMENSIONAL STRUCTURES

(75) Inventor: James D. Jacobson, Lindenhurst, IL (US)

(73) Assignee: Baxter International, Inc., Deerfield, IL (US)

( * ) Notice: Subject to any disclaimer, the term of this patent is extended or adjusted under 35 U.S.C. 154(b) by 169 days.

(21) Appl. No.: 10/167,890

(22) Filed: Jun. 12, 2002

(65) Prior Publication Data

US 2002/0162791 A1 Nov. 7, 2002

Related U.S. Application Data

(63) Continuation-in-part of application No. 09/457,173, filed on Dec. 8, 1999.

(51) Int. Cl.
*B01D 67/00* (2006.01)

(52) U.S. Cl. .................. 264/400; 264/1.38; 264/1.6; 264/1.7; 264/488

(58) Field of Classification Search ................ 210/483, 210/488, 489, 496, 500.21, 500.39; 264/1.37, 264/1.38, 1.6, 1.7, 400, 401, 488
See application file for complete search history.

(56) References Cited

U.S. PATENT DOCUMENTS

| 4,604,208 A | 8/1986 | Chu et al. |
| 4,797,175 A | 1/1989 | Ellion et al. |

(Continued)

FOREIGN PATENT DOCUMENTS

| EP | 0325752 A1 | 8/1989 |
| WO | WO 95/13860 | 5/1995 |
| WO | WO 96/10966 | 4/1996 |
| WO | WO 98/13131 | 4/1998 |
| WO | WO 99/64580 A1 | 12/1999 |
| WO | WO 00/05166 A1 | 2/2000 |
| WO | WO 00/16833 A1 | 3/2000 |
| WO | WO 01/41905 A1 | 6/2001 |

OTHER PUBLICATIONS

Ehrfeld et al., "Microfabrication of Membranes with Extreme Porosity and Uniform Pore Size," Journal of Membrane Science, 36, 1988, pp. 67–77.

Stemme et al., "New Fluid Filter Structure in Silicon Fabricated Using a Self–Aligning Technique," Appl. Phys. Lett. 53, 16, Oct. 17, 1988, pp. 1566–1568.

Wilding et al., "Manipulation and Flow of Biological Fluids in Straight Channels Micrhmachined in Silicon," Clinical Chemistry, vol. 40, No. 1, 1994, pp. 43–47.

"Microfabrication Technology for Research and Diagnostics," Brochure for Seminar by Cambridge Healthtech Institute, Sep. 28–29, 1995.

(Continued)

*Primary Examiner*—John Kim
(74) *Attorney, Agent, or Firm*—Austin J. Foley; Senniger Powers

(57) ABSTRACT

A method of manufacturing a three dimensional structure. In one embodiment, such structures comprise porous structures suitable for implantation in a host. Such a structure preferably exhibits geometric properties that tend to promote vascularization in the area of the structure when implanted into a host. The method includes selectively applying and exposing layers of biocompatible photoimageable material to create layers forming a cross-linked latticework structure having the desired geometric properties. Each layer is formed on top of a prior layer, preferably before any layer is developed. In one form, the structure is manufactured in connection with an implant device and promotes vascularization that supports bioacceptance/biocompatibility of the implant device.

52 Claims, 14 Drawing Sheets

U.S. PATENT DOCUMENTS

| | | |
|---|---|---|
| 4,797,211 A | 1/1989 | Ehrfeld et al. |
| 4,872,888 A * | 10/1989 | Ehrfeld et al. ......... 210/500.35 |
| 4,923,608 A | 5/1990 | Flottmann et al. |
| 5,256,360 A | 10/1993 | Li |
| 5,259,737 A | 11/1993 | Kamisuki et al. |
| 5,275,725 A | 1/1994 | Ishii et al. |
| 5,277,556 A | 1/1994 | van Lintel |
| 5,294,145 A | 3/1994 | Cheng |
| 5,348,788 A | 9/1994 | White |
| 5,427,663 A | 6/1995 | Austin et al. |
| 5,492,551 A | 2/1996 | Wolfe |
| 5,514,150 A | 5/1996 | Rostoker |
| 5,514,378 A | 5/1996 | Mikos et al. |
| 5,543,046 A | 8/1996 | Van Rijn |
| 5,651,900 A | 7/1997 | Keller et al. |
| 5,653,687 A | 8/1997 | Mills et al. |
| 5,681,568 A | 10/1997 | Goldin et al. |
| 5,705,070 A | 1/1998 | Saaski et al. |
| 5,709,798 A | 1/1998 | Adiletta |
| 5,711,960 A | 1/1998 | Shikinami |
| 5,714,160 A | 2/1998 | Magruder et al. |
| 5,728,089 A | 3/1998 | Lal et al. |
| 5,753,014 A | 5/1998 | Van Rijn |
| 5,770,076 A | 6/1998 | Chu et al. |
| 5,798,042 A | 8/1998 | Chu et al. |
| 5,807,406 A | 9/1998 | Brauker et al. |
| 5,824,204 A | 10/1998 | Jerman |
| 5,839,467 A | 11/1998 | Saaski et al. |
| 5,843,069 A | 12/1998 | Butler et al. |
| 5,849,208 A | 12/1998 | Hayes et al. |
| 5,855,801 A | 1/1999 | Lin et al. |
| 5,876,187 A | 3/1999 | Afromowitz et al. |
| 5,876,452 A | 3/1999 | Athanasiou et al. |
| 5,919,364 A | 7/1999 | Lebouitz et al. |
| 5,922,210 A | 7/1999 | Brody et al. |
| 5,928,207 A | 7/1999 | Pisano et al. |
| 5,928,880 A | 7/1999 | Wilding et al. |
| 5,938,923 A | 8/1999 | Tu et al. |
| 5,985,164 A | 11/1999 | Chu et al. |
| 5,985,328 A | 11/1999 | Chu et al. |
| 5,997,263 A | 12/1999 | Van Lintel et al. |
| 6,044,981 A | 4/2000 | Chu et al. |
| 6,129,928 A | 10/2000 | Sarangapani et al. |
| 6,146,771 A | 11/2000 | Wirt et al. |
| 6,180,129 B1 | 1/2001 | Magruder et al. |
| 6,187,329 B1 | 2/2001 | Agrawal et al. |
| 6,227,809 B1 | 5/2001 | Forster et al. |
| 6,333,029 B1 | 12/2001 | Vyakarnam et al. |
| 6,344,061 B1 | 2/2002 | Leitao et al. |
| 6,500,751 B2 * | 12/2002 | Surprenant et al. ......... 438/622 |
| 6,520,997 B1 * | 2/2003 | Pekkarinen et al. ..... 623/23.72 |

OTHER PUBLICATIONS

Van Rijn et al., "Micro Filtration Membrane Sieve with Silicon Micro Machining for Industrial and Biomedical Applications," Institute of Electrical and Electronics Engineers 1995, pp. 83–87.

Internet Posting: from "craum@marian.engg.uregina.ca" re: "Welcome to sci.engr.micromachining (FAQ)," Sep. 16, 1996.

Internet Posting: MSI Micron Separations Inc., www.msi-filters.com/msi_p24.htm, Oct. 22, 1996.

"Second Annual Microfabrication Technology for Biomedical Applications," Brochure for Seminar by Cambridge Healthtech Institute, Oct. 24–25, 1996.

DeJule, "Lithography News," Semiconductor International, Mar. 1997, p. 56.

Madou, Fundamentals of Microfabrication, 1997.

Yang et al., "Micromachined Membrane Particle Filters," MEMS 98 Workshop on Micro Electro Mechanical Systems, Jan. 25–29, 1998.

Hsiai et al., "Micro Fluidic Separation by Membrane Filters," Microsystems Technology in Medicine and Bioloby Seminar, Apr. 15–16, 1998.

"Micromechanics Europe '98 Posters," Micromachine Devices, Oct. 26, 1998.

Van Rijn et al., Internet Posting: "Aquamarijn Micro Filtration B.V.," from www.el.utwente.nl/mesa/aquamarijn/property.htm, Oct. 27, 1998.

Banks, Internet Posting: "Introduction to Microengineering MEME Micromachines MST," Apr. 26, 1999.

Beirne, et al., "Microfabricated Polyimide Membrane Test Structures," Microfabrication Applications Laboratory, The University of Illinois at Chicago, 6 pages.

Nelson, et al., "Microfabrication of Porous Polyimide Membranes," Microfabrication Applications Laboratory, The University of Illinois at Chicago, 9 pages.

* cited by examiner

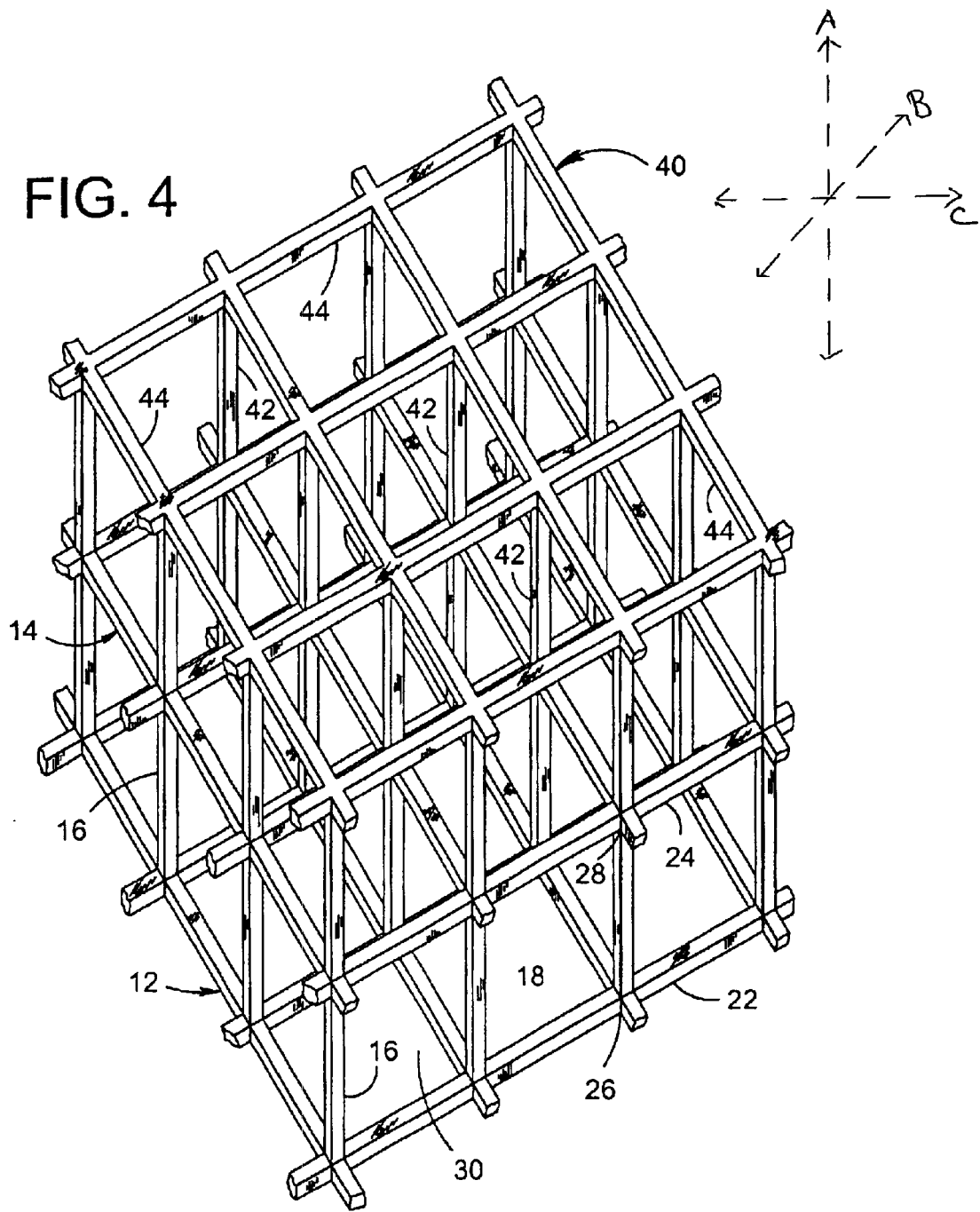

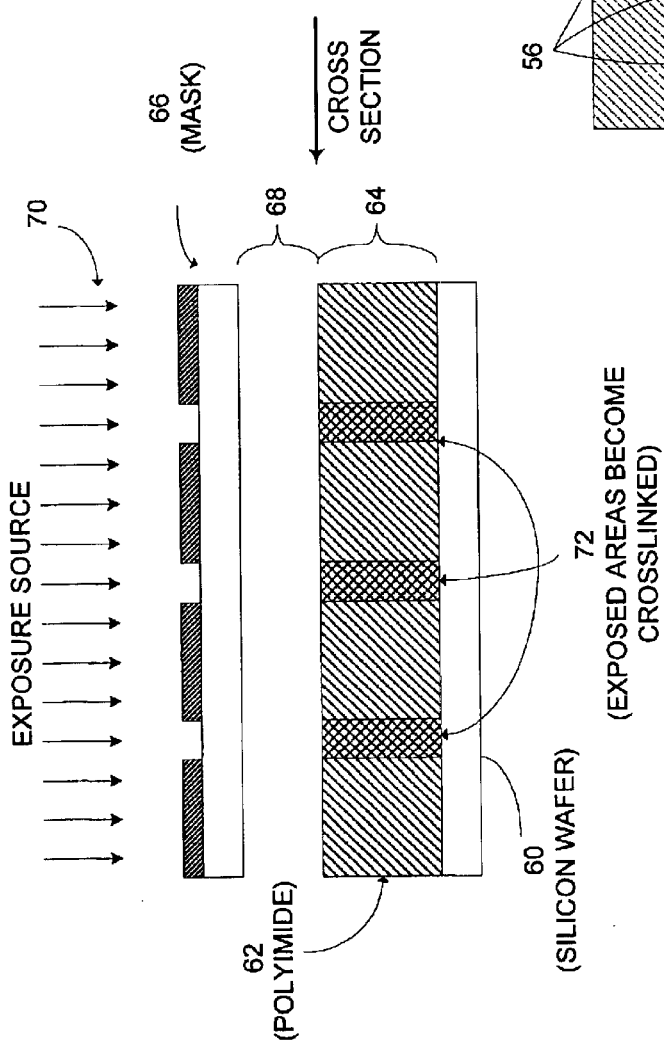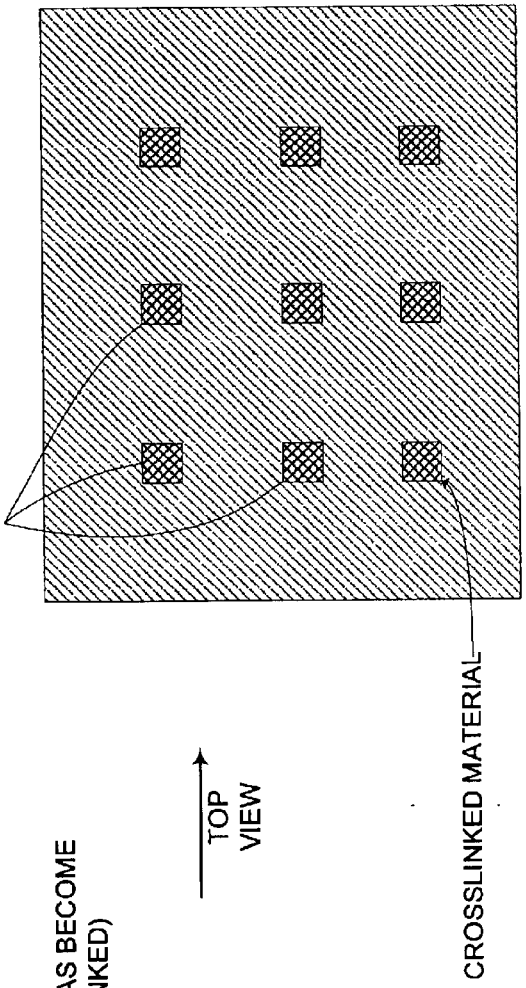

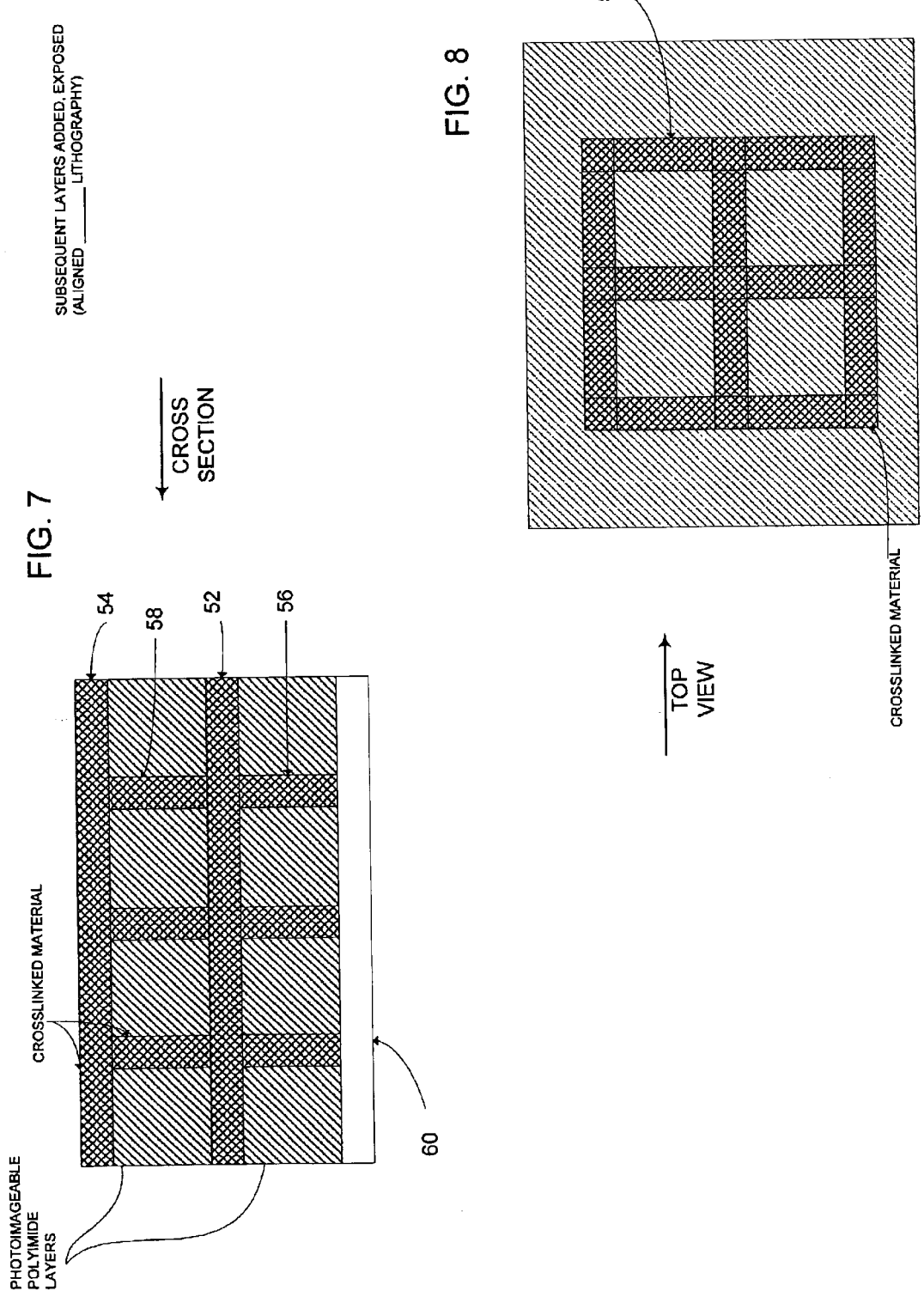

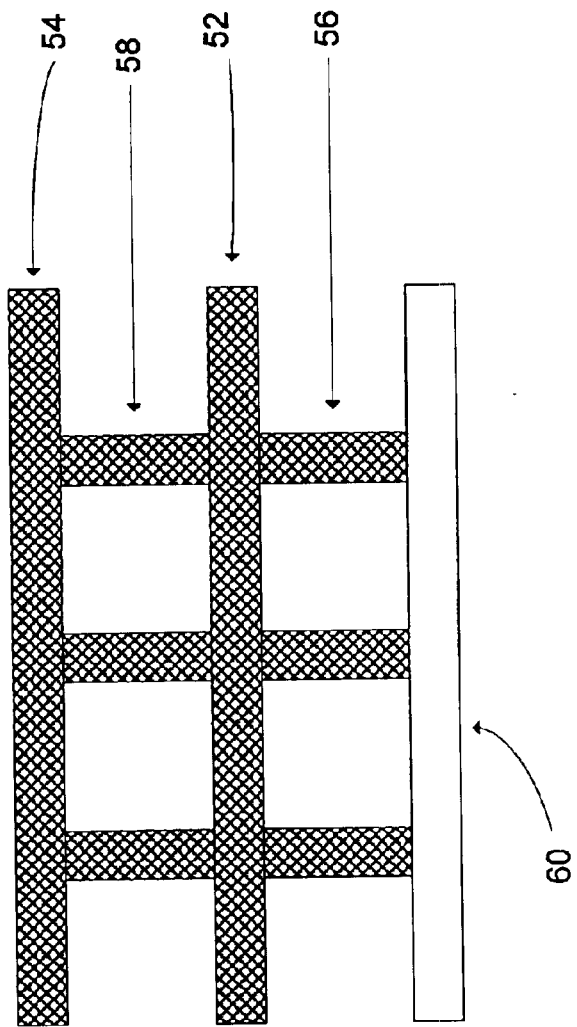

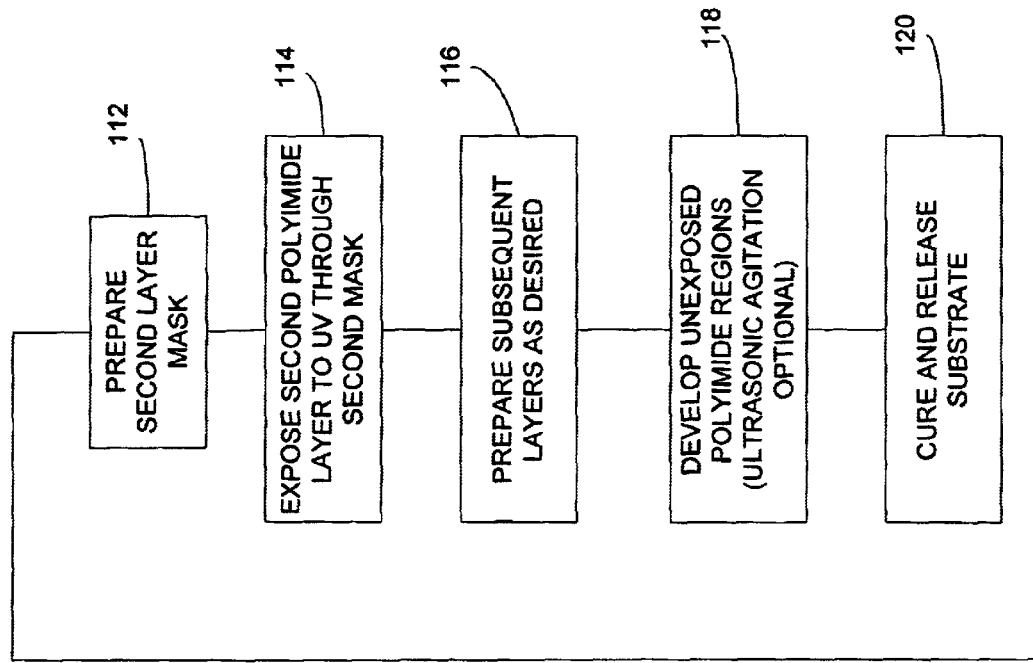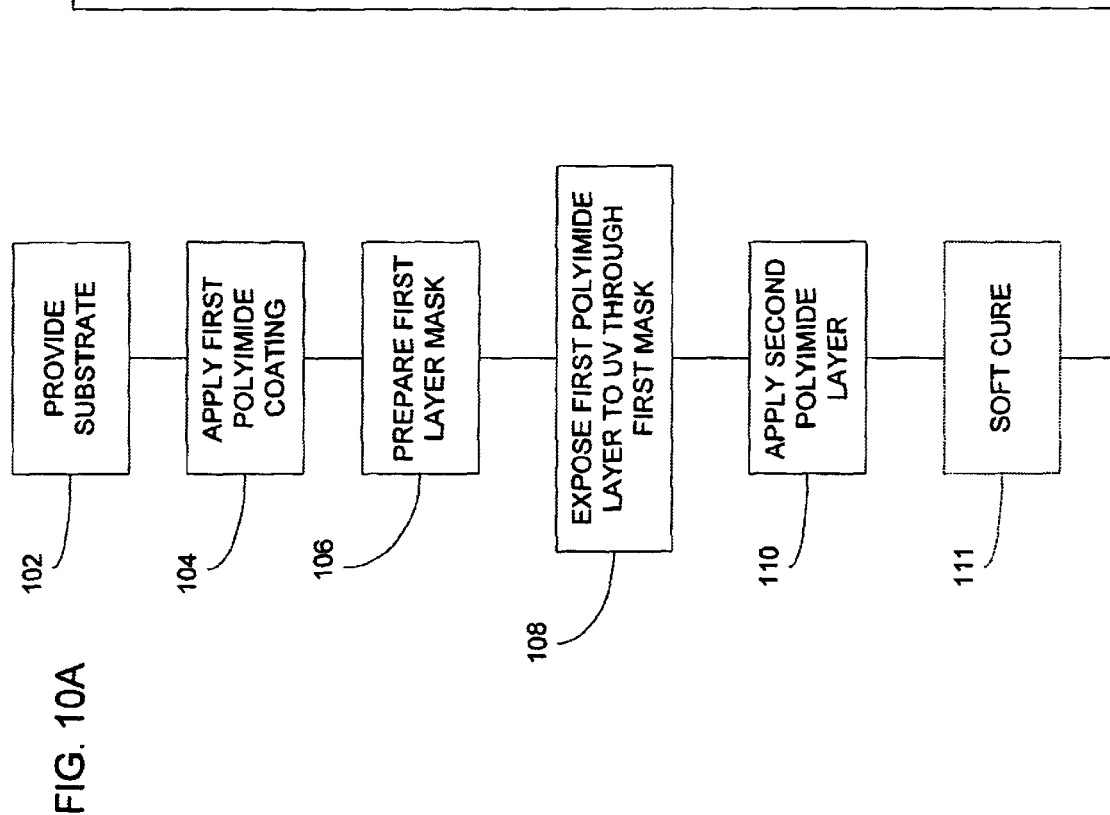
FIG. 10A

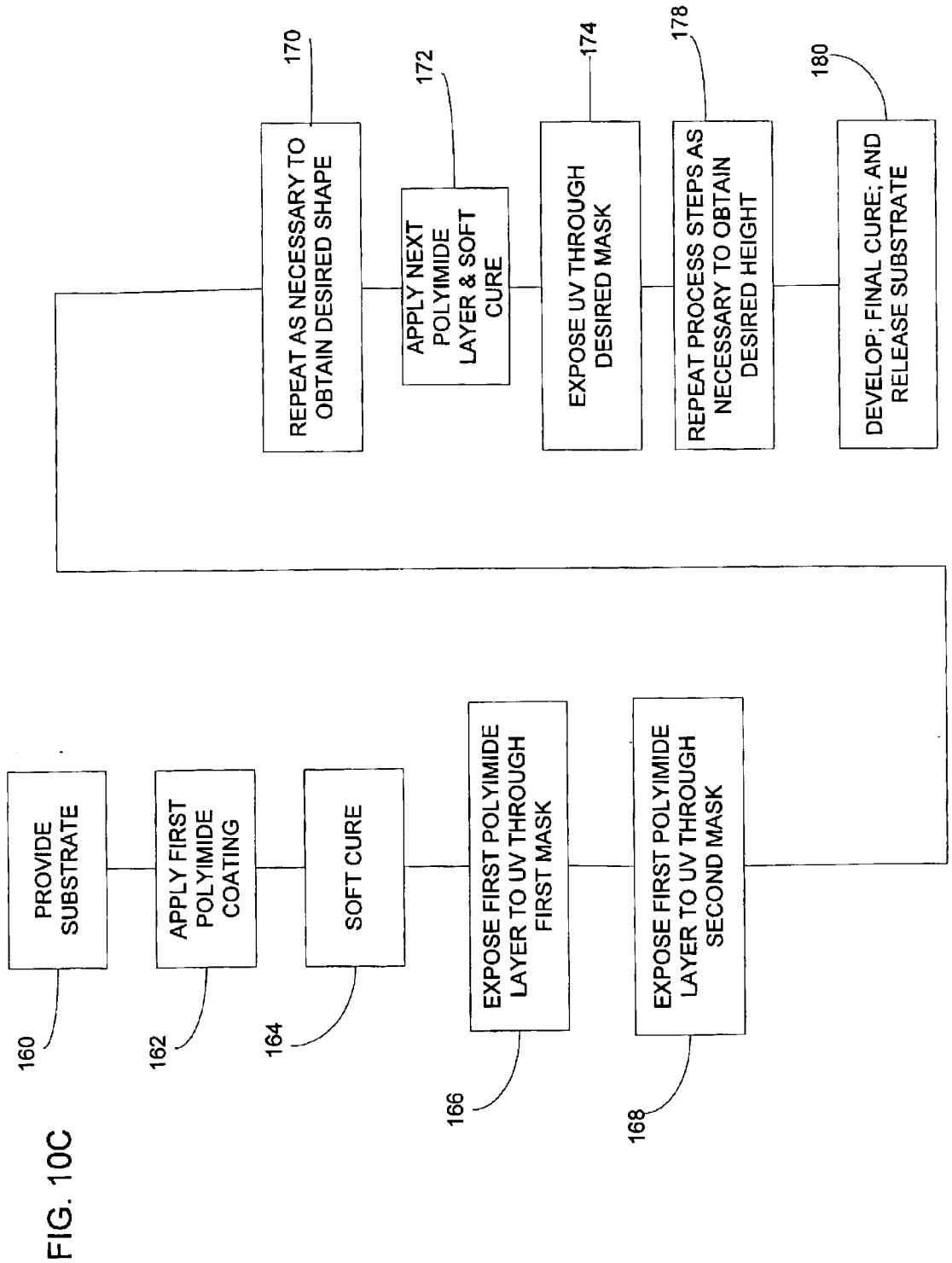

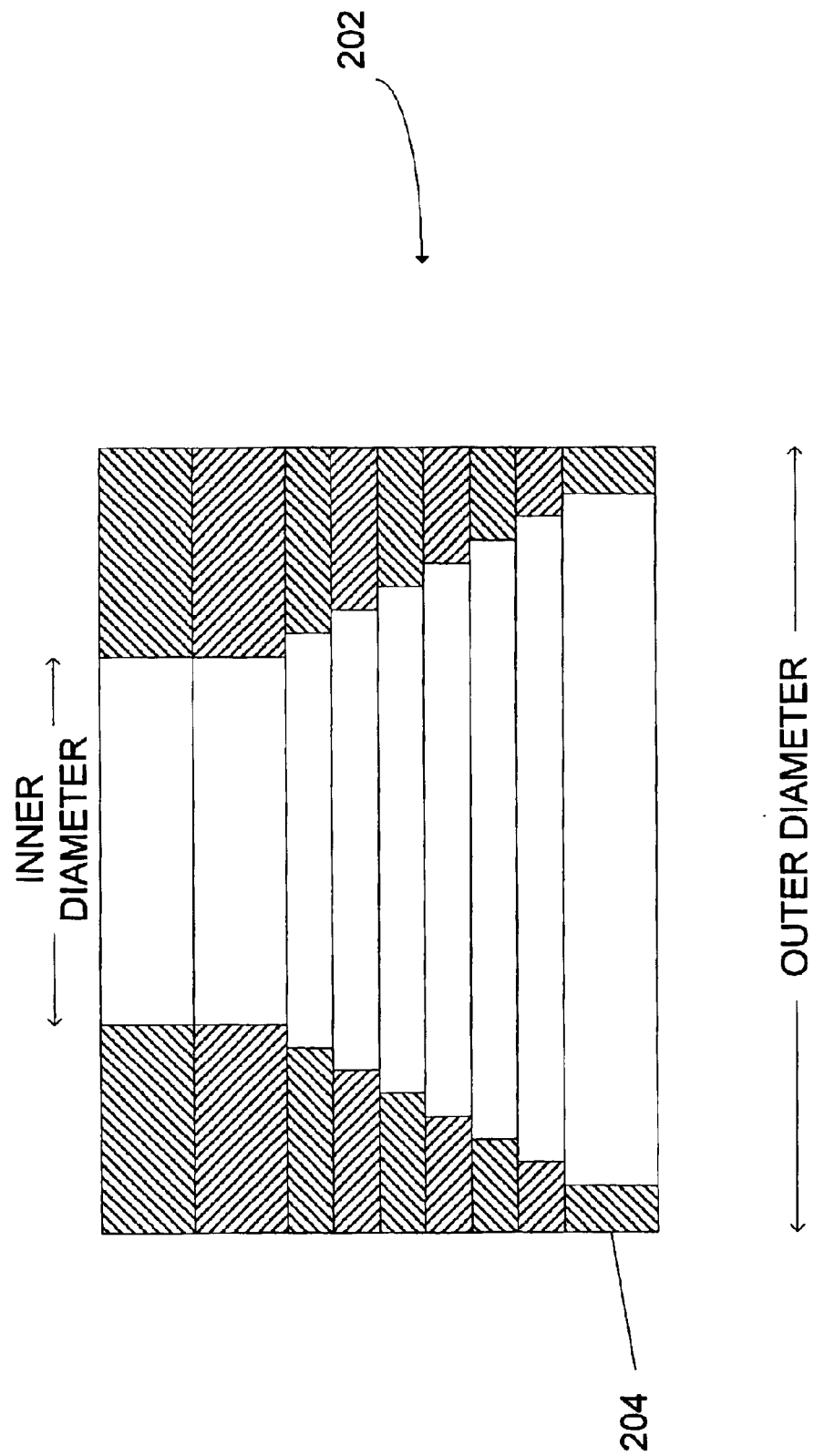

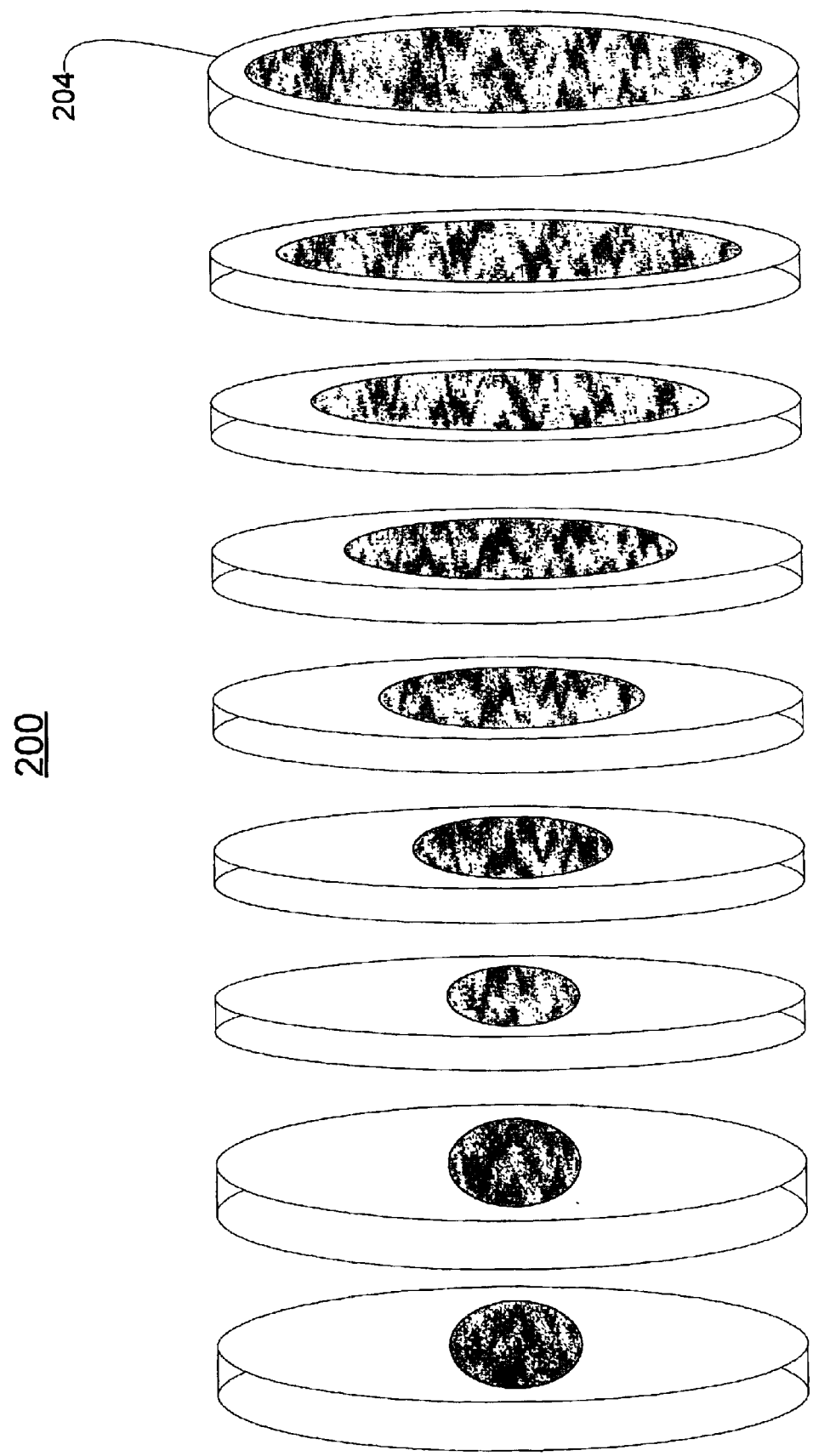

METHOD FOR FABRICATING THREE DIMENSIONAL STRUCTURES

CROSS REFERENCE TO RELATED APPLICATION

The invention of the present application is a continuation-in-part of U.S. patent application Ser. No. 09/457,173, filed on Dec. 8, 1999, the entire disclosure of which is incorporated herein by reference.

BACKGROUND OF THE INVENTION

1. Field of the Invention

The present invention relates generally to methods of fabricating three dimensional structures and, particularly, to methods of making three dimensional structures using a lithographic, layer-by-layer process. Such structures include porous three dimensional structures for use in applications where a reduced foreign body capsule formation and increased adjacent vascularization is desired, such as medical devices for permanent and temporary implantation.

2. Description of the Prior Art

Implantable medical devices with biological components are used for various purposes, such as indwelling chemical sensors, controlled drug-release systems, and biohybrid artificial organs for use with cellular therapies. See, for example, Colton, *Implantable Biohybrid Artificial Organs,* 4 Cell Transplant 415–36 (1995). All of these devices have in common the need for adequate perfusion of small and large molecules to or from the blood stream through the surrounding soft tissue. A serious problem in the development of devices for these applications is the formation of an avascular fibrous capsule around the implanted device. The capsule consists of (i) a layer of macrophages and/or foreign body giant cells at the material-tissue interface, overlain by (ii) an avascular region up to 100 μm thick containing layers of fibroblasts embedded in a collagen matrix, which in turn is overlain by (iii) a region of blood vessels and fibroblasts in a loose connective tissue matrix. Spector, et al., *The Local Tissue Response to Biomaterials,* 5 Crit. Rev. Biocompat. 269–95 (1989). This capsule creates extra diffusion distance between the vasculature and the device. In addition, the tissue capsule may have inherently poor transport properties, as evidenced by measurements of glucose permeation through fibrotic tissue capsules formed on silicone rubber implanted subcutaneously in rats. The effective diffusion coefficient though this capsule is estimated to be one to two orders of magnitude lower than the value in water, Freeman, et al., *A Study of the Mass Transport Resistance of Glucose Across Rat Capsular Membranes,* 110 Mater. Res. Soc. Symp. Proc. 773–78 (1989). This reduced diffusion of nutrients and oxygen through the foreign body fibrous capsule has deleterious effects on the viability and/or function of tissues implanted in a biohybrid artificial organ.

Brauker discovered that certain microporous materials, when implanted subcutaneously, induce permanent neovascularization at the interface with host tissue by virtue of their morphology and microarchitecture. Brauker, et al., *Neovascularization of Synthetic Membranes Directed by Membrane Microarchitecture,* 29 J. Biomed. Mat. Res. 1517–24 (1995). This result was observed with membranes made from a variety of polymers using diverse fabrication methods, including solvent evaporation and stretching. The fact that this behavior was observed for membranes of widely varying chemical composition indicates that microarchitecture, rather than chemistry, is of primary importance in stimulating macrophage migration and neovascularization. Light microscopy revealed that the materials that induce neovascularization have interstices or openings that allow host inflammatory cells, such as monocytes and macrophages, to invade the membrane. Furthermore, once inside the membrane, many of these cells retain a non-flattened morphology and do not adhere to the very thin structural elements of the material. A fibrous capsule overlying the vasculature at the interface may also form around these materials. Brauker observed that materials that produce a thick fibrous capsule without neovascularization at the material-tissue interface had either interstices which were too small for host inflammatory cells to invade, or interstices which were large enough for virtually all of the host cells that invade the membrane to adhere and flatten on the internal structural elements of the material, which provided sufficiently large internal area for cell adhesion. Brauker generally found an increase in inflammatory cell penetration and an increase in vascular structures adjacent to the membrane when the nominal membrane pore size was about 1.0 μm or larger.

Further, Padera demonstrated that the major events in the process of membrane microarchitecture-driven neovascularization occur within the first week of implantation. Padera, et al., *Time Course of Membrane Microarchitecture-driven Neovascularization,* 17 Biomaterials 277–84 (1996). Host inflammatory cells migrate into the membrane after three days of implantation. Their number increases for seven days, remains constant through 21 days and decreases by roughly half at 329 days. Blood vessels are found closer to the material-tissue interface with increasing time over the first week post-implantation. The vessels first arrive at the interface after three days, increasing rapidly through ten days, and then increase slowly through 21 days. The density of close vascular structures at the interface remained virtually constant after 21 days through 11 months, the duration of Padera's experiment. Fibrous capsule formation starts as early as seven days post-implantation, and the capsule continues to mature until the fibroblasts die or migrate away to leave a nearly acellular, scar-like collagen matrix.

These results correlate with the course of events seen in normal wound healing. In normal wound healing, neutrophils are the predominant cell type at the site of injury within the first 24–48 hours, killing and phagocytosing any bacteria present. The macrophage becomes the predominant cell after this time, removing cellular and foreign debris from the area. Within three to four days, fibroblasts migrate out of the surrounding connective tissue into the wound area and begin to synthesize collagen, which quickly fills the wound space. New blood vessels begin to grow into the area at this time to supply oxygen and nutrients needed by the metabolically active fibroblasts and macrophages in the wound. An important difference between normal wound healing and membrane microarchitecture-driven neovascularization is that in normal wound healing the vessels begin to regress in the second week, but in membrane microarchitecture-driven neovascularization the vessels remain at the interface. Although the mature scar is avascular and acellular in a normal wound, in membrane microarchitecture-driven neovascularization, a multitude of vessels persist at the material-tissue interface in an otherwise largely acellular scar. This persistent adjacent vascular structure would be useful for maintaining the nutrient and oxygen supply to, and thus the viability of, the biological components of artificial organ devices.

These initial experiments which demonstrated the neovascularizing microarchitectural effect used membranes whose surface structure size and spacing were randomly generated, thereby producing an irregular structure. Commonly owned U.S. Pat. No. 5,807,406 (the disclosure of which is incorporated herein by reference) describes a microfabricated porous laminar structure for holding living cells composed of net-like layers of polymer with precisely defined and periodic holes. Although these structures are regular within the two dimensional plane of their laminar layers, they are irregular and sometimes compressed in the third dimensional plane. This creates a less well defined structure in which some interstices are blocked by strands of the polymer net from adjacent layers. Although these structures were also found to generally promote neovascularization at the structure/tissue interface upon implantation into animals, the "blocked" interstices did not allow invasion of those portions of the structure by inflammatory cells.

U.S. Pat. No. 5,797,898 discloses implantable microchip drug delivery devices for controlling the rate and time of release of multiple chemical substances and molecules. Other systems and methods in the prior art disclose biocompatible structures for implantation in general, but fail to disclose structures that can be precisely formed in multiple dimensions. For example, some prior art techniques rely on biocompatible foams for fabricating an implantable structure. For some applications, such structures are sufficient. In other applications, however, precise control of the various internal structural dimensions is important, and such foams provide insufficient dimensional control.

Commonly assigned U.S. patent application Ser. No. 09/731,486, filed Dec. 7, 2000, by Pekkarinen and Brauker (hereinafter "the Pekkarinen et al. application"), discloses a porous, three dimensional structure for use in applications where a reduced body capsule formation and increased adjacent vascularization is desired. The Pekkarinen et al. application reflects substantial improvements over the above-described art. The entire disclosure of the Pekkarinen et al. application is incorporated herein by reference.

It is also known in the art to use rapid prototyping and stereolithographic techniques to create three dimensional structures. One prior art process involves creating a mask layer for a broad field exposure of resin for each layer and requires a large, complex machine. Other approaches use so-called "laser-writing" of resins to create each layer, with the layers created lowered to accommodate the next resin layer. These prior art techniques, however, do not allow for layer-by-layer fabrication having sufficient control over layer thickness and layer feature resolution (e.g., with respect to the two-dimensional pattern reflected in that layer) to produce structures similar to those disclosed in the Pekkarinen et al. application.

SUMMARY OF THE INVENTION

Although the invention disclosed and claimed in the Pekkarinen et al. application represents substantial improvements in the art, further improvements are desired. For example, it is considered to be advantageous to produce structure similar to those described in the Pekkarinen et al. application by different approaches. One such approach includes reducing the number of process steps necessary. Further, improvements may also be desired with additional layers. Other improvements include providing greater control of the final structure in terms of both two dimensional control and three dimensional control.

Briefly described, in one aspect, the invention relates to a method of manufacturing a three dimensional structure having at least a first layer and a second layer. The method comprises providing a substrate layer. A first coating of a photoimageable material is applied to the substrate layer. A first mask is prepared having a pattern corresponding to the first layer of the three dimensional structure to be manufactured. The first coating of the photoimageable material is exposed with an exposure source through the first mask such that the first layer of the three dimensional structure is provided. A second coating of the photoimageable material is applied subsequent to the first layer of the three dimensional structure. A second mask is prepared having a pattern corresponding to the second layer of the three dimensional structure to be manufactured. The second coating of the photoimageable material is exposed with the exposure source through the second mask such that the second layer of the three dimensional structure is provided. The regions of said first and second coatings that do not correspond to a layer of the three dimensional structure are developed and removed.

In another aspect, the invention relates to a method of fabricating a three dimensional structure having at least a first layer and a second layer. The method comprises providing a substrate layer. A first coating of photoimageable material is applied at a position subsequent to the substrate layer. A first mask is prepared having a pattern corresponding to at least a first portion of the first layer of the three dimensional structure to be fabricated. The first coating is exposed with an exposure source through the first mask such that at least a first portion of the first layer is formed. A second coating of photoimageable material is applied subsequent to the first layer. A second mask having is prepared a pattern corresponding to at least a first portion of the second layer of the three dimensional structure to be fabricated. The second coating is exposed with the exposure source through the second mask such that at least a first portion of the second layer is formed. A developing process is applied to remove regions of the photoimageable material that do not correspond to the first and second layers.

In still another aspect, the invention is directed to a method of fabricating a structure for implantation in a host. The structure includes a porous three dimensional structure having at least first and second layers and being sized and shaped for producing an inflammatory foreign body response. At least one of the first and second layers has a plurality of openings sized to permit fluid and inflammatory cells of the host to pass through the openings and migrate into an interior volume of the porous thee dimensional structure, and sized to promote a non-flattened morphology of the inflammatory cells. The porous three dimensional structure promotes vascularization adjacent said structure when implanted into the host. The method comprises providing a microfabricated medical implant device constructed and arranged for implantation in the host. The microfabricated sensor comprises a substrate layer onto which the porous three dimensional structure can be fabricated. A first coating of photoimageable material is applied to the substrate layer. A first mask is prepared having a pattern corresponding to at least a first portion of the first layer of the three dimensional structure to be fabricated. The first coating is exposed with an exposure source through the first mask such that at least a first portion of the first layer is formed. A second coating of photoimageable material is applied subsequent to the first layer. A second mask is prepared having a pattern corresponding to at least a first portion of the second layer of the three dimensional structure to be fabricated. The second coating is exposed with the exposure source through the second mask such that at least a first portion of the second layer is formed. A developing process is applied to remove regions of the photoimageable material that do not correspond to the first and second layers.

In yet another aspect, the invention relates to a method of fabricating a three dimensional structure having a plurality of layers. The method comprises providing a substrate. A first coating of photoimageable material is applied at a position subsequent to the substrate. A first mask is prepared having a pattern corresponding to at least a first portion of one of the plurality of layers of the three dimensional structure to be fabricated. The first coating is exposed with an exposure source through the first mask such that at least a first portion of the one of the plurality of layers is formed. A second coating of photoimageable material is applied subsequent to the first coating and after exposing the first coating with the exposure source. The second coating is exposed with the exposure source through the first mask such that at least a second portion of the one of the plurality of layers is formed.

In other aspects, the invention relates to three dimensional structures manufactured according to the processes disclosed herein, including biocompatible structures having porous three dimensional structures sized to promote vascularization adjacent the structure when implanted in a host. In one form, the structure also includes an implant device associated with the three dimensional structure such that the three dimensional structure promotes vascularization adjacent the implant device.

Alternatively, the invention may comprise various other devices, methods, and systems.

Other objects and features will be in part apparent and in part pointed out hereinafter.

BRIEF DESCRIPTION OF THE DRAWINGS

FIG. 4 is a fragmentary perspective of another exemplary three dimensional structure manufactured in accordance with aspects of the present invention.

FIGS. 5–9 are schematic views of a process of manufacturing porous three dimensional structures, such as the exemplary structures illustrated in FIGS. 1 and 4, in accordance with aspects of the present invention.

FIG. 10A is a flow chart illustrating pertinent steps of one exemplary method of fabricating three dimensional structures in accordance with aspects of the present invention.

FIG. 10C is a flow chart illustrating pertinent steps of another exemplary method of fabricating three dimensional structures, in accordance with aspects of the present invention, including using different masks in connection with preparing one layer.

FIG. 12 is a schematic representation of a three dimensional structure corresponding to a nozzle, fabricated in accordance with aspects of the present invention.

FIG. 13 is an exploded view of the nozzle schematically depicted in FIG. 12.

Corresponding reference characters indicate corresponding parts throughout the drawings.

DETAILED DESCRIPTION OF PREFERRED EMBODIMENTS

In general, U.S. patent application Ser. No. 09/457,173, which is incorporated herein by reference and to which the present application claims priority, discloses microporous filter membranes and methods of making such membranes. More specifically, this application discloses a filter having a monolithic polymeric filter layer, including micron-scale precision-shaped pours, and a polymeric support layer. One of the methods for making filter membranes disclosed therein includes spinning a first layer of polyimide onto a silicon wafer. This first layer is exposed to a light source through a mask defining a pattern of one of the micron-scale pores or the support structure. A second polyimide layer is thereafter spun onto the first layer so as to create an interface therebetween. The second polyimide layer is then exposed to a light source through a mask defining a second pattern of another of the micron-scale pores or the support structure. Selected material is removed from the first and second polyimide layers to define micron-scale pores and support structure. The first and second polyimide layers are cured together so as to remove the interface therebetween and create a monolithic filter layer-support structure.

Figure 1:
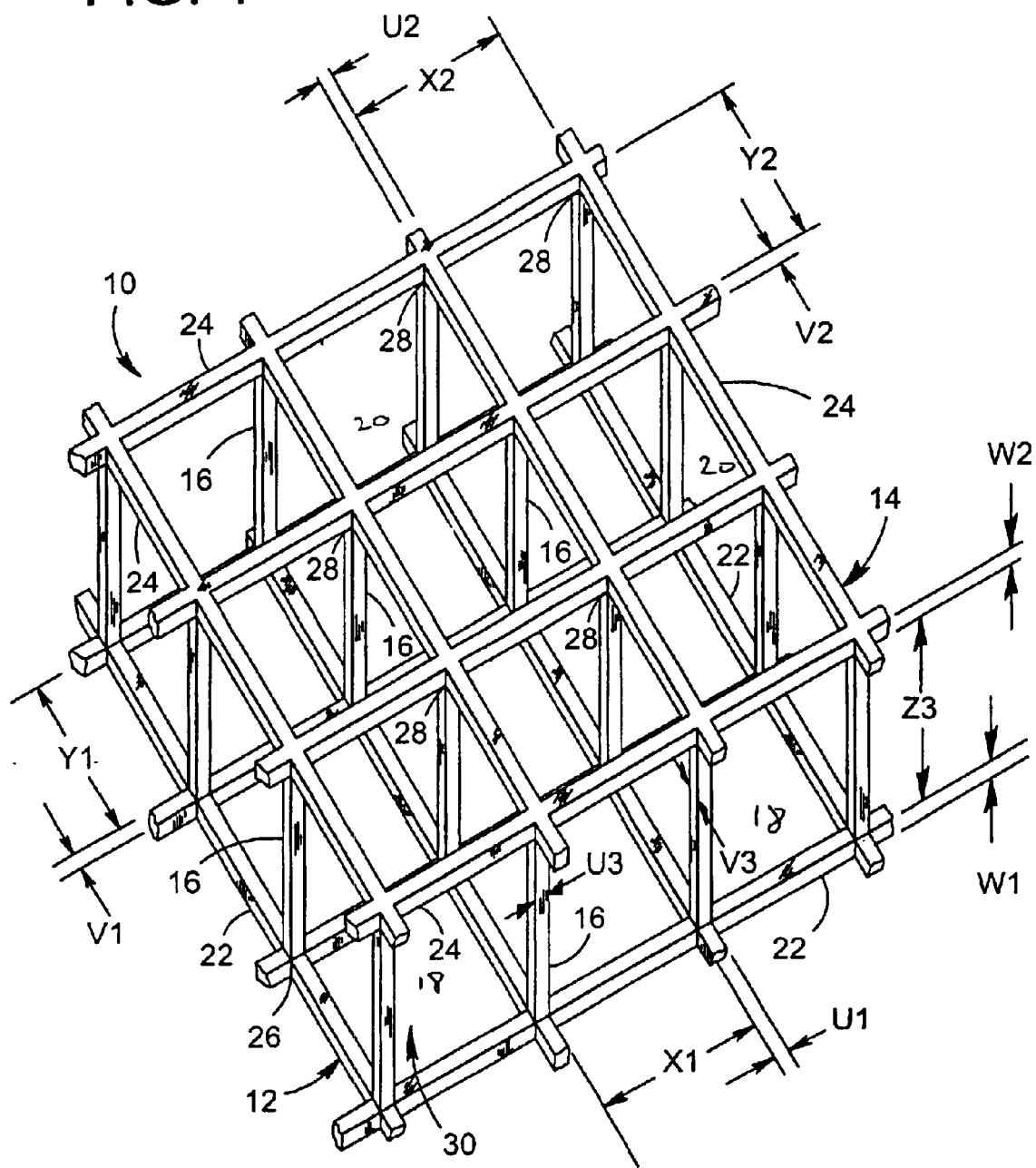
FIG. 1 is a fragmentary perspective of an exemplary three dimensional structure manufactured in accordance with aspects of the present invention.

Referring now to the drawings, FIG. 1 is a fragmentary perspective of an exemplary porous three dimensional structure, manufactured in accordance with aspects of the present invention. Such a structure is suited for temporary and/or permanent implantation in a host capable of producing an inflammatory foreign body response, such hosts include human beings and other animals. The exemplary structure illustrated in FIG. 1 has a first girder layer 12, a second girder layer 14, and a post layer 16 connecting the first and second girder layers 12, 14.

In the illustrated embodiment, each girder layer 12, 14 has a plurality of openings 18, 20. In one embodiment, the openings of each girder layer are aligned with the openings of the other girder layers, and each of the posts of post layer 16 are substantially identical in length. The openings are sized and shaped to permit fluids and inflammatory cells of the host animal to pass through the openings and migrate into an interior volume of the porous three dimensional structure. Although FIG. 1 illustrates generally square openings, it should be appreciated that the openings may have other shapes, uniform and non-uniform. Further, posts of different lengths and shapes can also be used. A girder layer coupled with a post layer may sometimes be referred to as a scaffold. In the illustrated embodiment, each of the posts of post layer 16 have substantially the same length and are positioned substantially normal to each girder layer 12, 14, thereby defining a structure that is substantially symmetric in three dimensions.

In one embodiment, the openings are sized within tolerances such as those disclosed in the Pekkarinen et al. application (U.S. patent application Ser. No. 09/731,486). As explained in that application, it is believed that openings of particular sizes allow inflammatory cells invading the structure to adhere to strands forming the openings in multiple planes. Such three dimensional adherence prevents the cells from assuming a flattened, spread morphology. As further explained in the Pekkarinen et al. application, it is believed that such a morphological change is an early step in the inflammatory foreign body response cascade. When non-flattened inflammatory cells remain in the porous three dimensional structure, the appearance and persistence of close vascular structures adjacent the implanted material is observed. It is further believed that the invading inflammatory cells release an angioneogenic signal molecule that encourages growth or migration of vascular structures close to the implanted structure. Thus, the size of the openings 18, 20 and the length of the posts of post layer 16 are preferably selected to promote a non-flattened morphology of the cells of interest.

Figure 2:
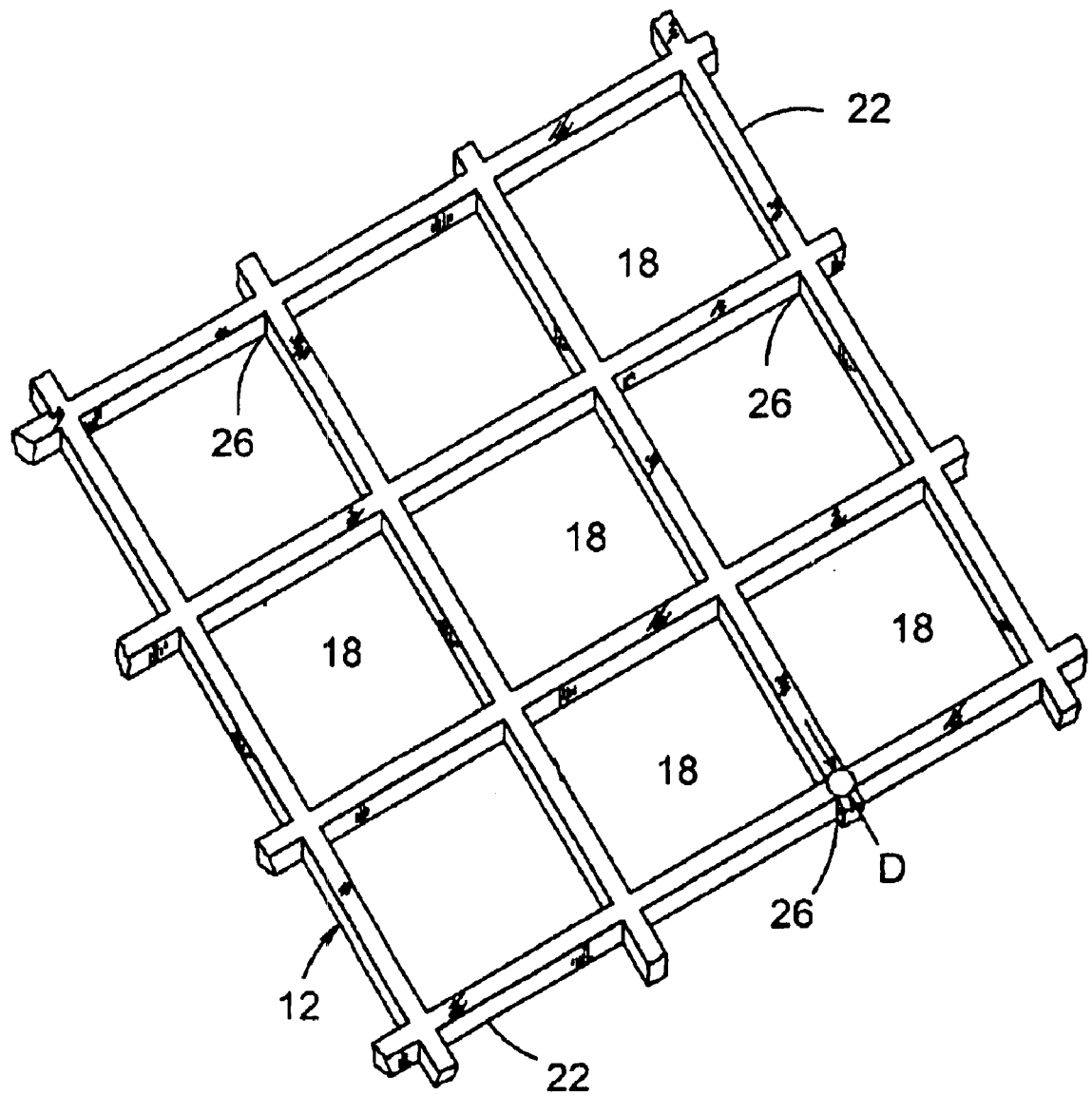
FIG. 2 is a fragmentary perspective of a girder layer of the structure illustrated in FIG. 1.

FIG. 2 is a fragmentary perspective of an exemplary girder layer, such as a girder layer of the porous three dimensional structure illustrated in FIG. 1.

Figure 3:
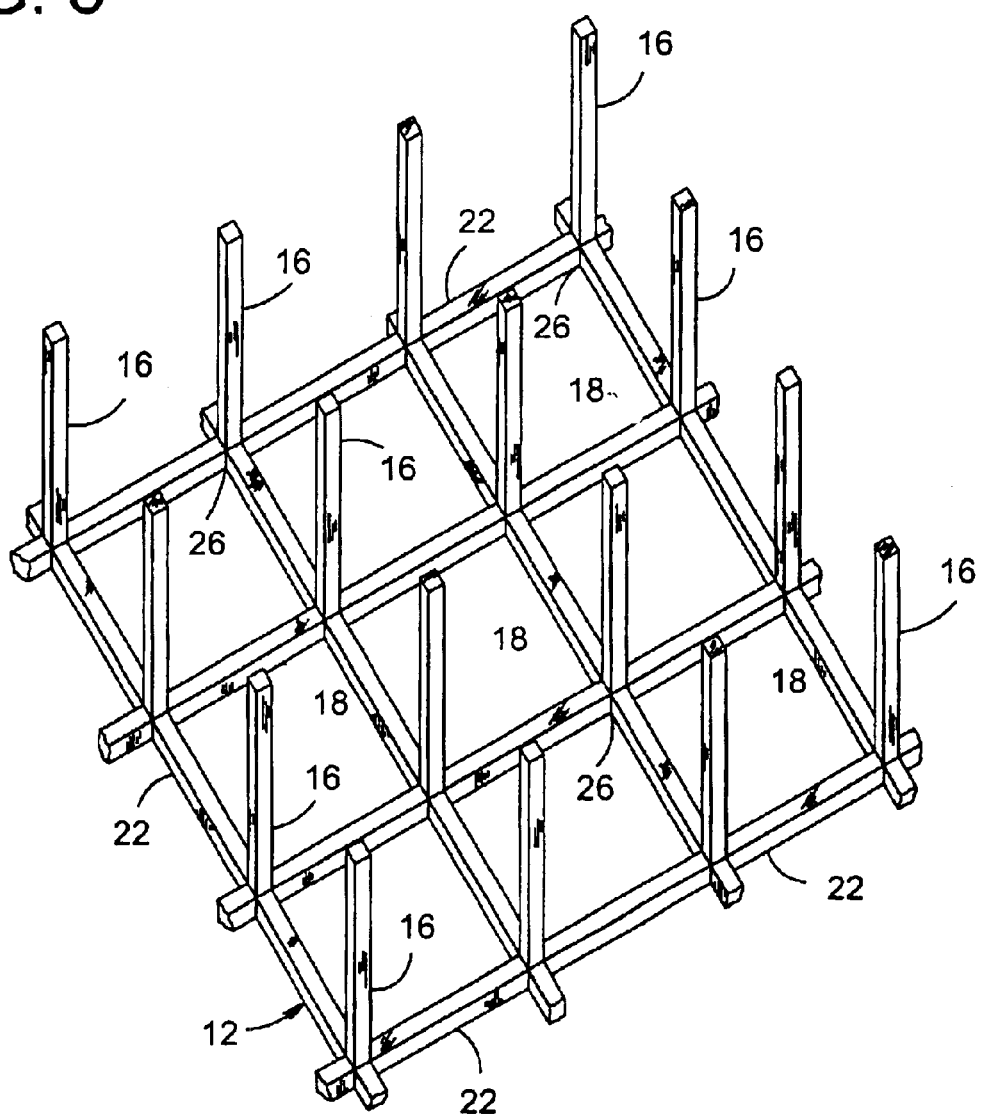
FIG. 3 is a fragmentary perspective of the first layer and a plurality of posts of the structure illustrated in FIG. 1.

FIG. 3 is a fragmentary perspective of the girder layer 12 and the post layer 16 of the structure illustrated in FIG. 1.

FIG. 4 is a fragmentary perspective of another exemplary porous three dimensional structure manufactured in accordance with aspects of the present invention. In particular, FIG. 4 illustrates such a structure having three girder layers 12, 14, and 40, connected by two post layers 16 and 42. In one preferred embodiment, each of the three girder layers 12, 14, 40 are substantially symmetrical; and the two post layers 16 and 42 are also substantially symmetrical to each other. As used herein substantially symmetrical is intended to include having generally the same dimensions, within desired manufacturing tolerances. The dashed lines A, B, and C are intended to indicate that the periodic structure could continue in all three dimensions.

FIGS. 5–9 are schematic views of a process of manufacturing porous three dimensional structures, such as the structures illustrated in FIGS. 1 and 4, in accordance with aspects of the present invention. FIGS. 5–9 illustrate the steps for manufacturing an exemplary porous three dimensional structure having two girder layers (indicated generally in FIG. 9 by references 52, 54) and two post layers (indicated generally in FIG. 9 by references 56, 58). FIGS. 5 and 6 illustrate the pertinent steps associated with preparing a first post layer 56. FIG. 5 depicts a view of one cross-section of the first post layer 56. FIG. 6 depicts a top view of first post layer 56. FIGS. 7 and 8 illustrate the addition of girder layers 52, 54, and second post layer 58. In particular, FIG. 7 illustrates one cross-sectional view of the structure, and FIG. 8 illustrates a top view, from the perspective of second girder layer 54. It should be understood that the basic steps associated with each layer are generally the same; differences between preparing subsequent layers are discussed, as necessary, herein.

As shown in FIG. 5, the porous three dimensional structure starts with a substrate layer 60. In one embodiment, the substrate layer 60 comprises a silicon wafer, such as a wafer suitable for use in semiconductor manufacturing processes. Other substrate materials include, for example, glass, quartz, and plastic. An advantage of silicon is that silicon is readily available in the form of wafers having very good quality characteristics (e.g., extremely flat). Further, there are many resources available for silicon processing. Still another advantage of working with silicon is that micro electromechanical system (MEMS) devices can be made within the silicon substrate (e.g., to accompany the three dimensional structure). Silicon also has a native oxide that can be etched in hydrofluoric acid based solutions, thereby simplifying processing. When using non-silicon materials as a substrate, however, one or more sacrificial layers may be provided between the structural layers and the substrate. The sacrificial layer allows etching or other techniques to allow release of the structure fabricated.

A layer of a photoimageable material is applied to substrate layer 60 (or the sacrificial layer) by processes that are known in the art. If the structure is destined for a medical use, such as implantation in a host, the photoimageable material preferably comprises a governmentally approved biocompatible material. For example, a biocompatible photoimageable material in one embodiment comprises an approved polyimide that is applied in spincoat fashion on substrate layer 60 to a rib thickness 64 corresponding to the desired height/thickness of the layer to be produced (e.g., post layer 56). Rib thickness generally refers to layer thickness.

HD MicroSystems, LLC, offers a range of photodefineable polyimide products, suitable for use in connection with certain aspects of the present invention, having various process parameters and development and rinse solutions. For example, a series sold as the PI 2770 series comprises a negative tone material, using G-line or I-line exposure, and development in a tetramethylammonium hydroxide (TMAH) solution with a water rinse. Typical film thicknesses for the PI 2770 series is around 4–9 microns. Thicknesses in this range can be obtained from the same grade of product by adjusting the rotational rate of the substrate during spin coating from less than about 1000 RPM to about 6000–7000 RPM. A typical spin is around 60 seconds. HD MicroSystems also provides a negative tone 2730 series product that is suited for use in connection with aspects of the present invention. The 2730 series product allows film thicknesses from about 1 micron to about 12 microns, and uses G-line exposure and solvent development with a product available as DE 9040, followed by a rinse in a product available by the name RI 9180. Other product lines include positive tone, photodefineable polyimide materials, such as HD 8000 and HD 8001. As indicated above, when used in a medical context, such as implantation in a host, the photodefineable polyimide comprises a governmentally approved, biologically compatible material, having a structure similar to the exemplary materials discussed herein.

The Dow Chemical Company offers nonpolyimide photoimageable, polymer products under the mark CYCLOTENE which may be used in connection with certain aspects of the present invention. Arch Chemicals, Inc., offers products under the mark DURIMIDE, including 7000, 7500, and 7800 series products, that are also suitable for use in connection with aspect of the present invention.

G-line exposure comprises a 435 nm wavelength exposure source. I-line comprises a 365 nm exposure source. Exposure sources over 350 nm are generally regarded to be UV sources. Exposure sources on the order of 150–300 are generally regarded as DUV sources.

Polyimide application (i.e., spinning and so on) and certain other process steps can be accomplished using a multi-step system, such as the MTI TARGETRACK system, available from Machine Technology, Inc., of Parsippany, N.J.

In order to produce the desired structural characteristics of the layer of interest, a mask 66 is prepared. The mask 66 has a pattern that corresponds to a cross section of the layer to be produced. For example, when preparing a post layer, mask 66 preferably comprises a series of square and/or rectangular patterns corresponding in size and shape to the smallest two dimensions of the desired posts. In one embodiment, mask 66 comprises a chrome-layered, patterned quartz mask. With a suitable mask 66 prepared, the mask is positioned between wafer 60 and an exposure source 70 (e.g., a UV source, such as a UV exposure source on the order of 350 nm or more, or a DUV source between about 150 nm and 300 nm) at a distance 68 from the layer of photoimageable material 62 (e.g., polyimide). The mask allows the UV or DUV light to expose only portions 72 of photoimageable material 62. The exposed portions 72 of the photoimageable material 62 become cross-linked as a result of the exposure. As will be explained more below, unexposed portions of the photoimageable material 62 are later removed by a developing process which does not remove the cross-linked material.

The length of exposure for a given layer (sometimes referred to herein as exposure time) is included in a recipe for the structure being constructed. In general, exposure times include considerations of the thickness of the layer being produced and the photoimageable material being used. With the benefit of the present disclosure, it should now be understood that the precision required with respect to exposure times can vary, depending upon the layer under consideration. For example, exposing a girder layer too long can result in "penetrating" into and exposing photoimageable material from a lower/earlier layer (e.g. an unexposed portion of a lower post layer), thereby increasing the thickness of the current girder layer beyond the thickness of the current layer of photoimageable material. On the other hand, with symmetrical structures such as those illustrated in FIGS. 1 and 7, overexposing a post layer has less severe consequences because the overexposure simply reaches into a prior layer having the same form (i.e., it does not adversely impact the final structures geometry). In fact, in some applications, an exposure that "reaches into" a prior layer can be desirable because it allows cross-development to prior layers (e.g., allows posts to be cross-developed into prior layers).

To this point, photoimageable material 62 has been described in terms consistent with a "negative tone" material (sometimes referred to as a negative photoresist or an insoluble photoresist). With a negative photoresist, the patterns formed during exposure and development are the reverse (negative image) of the mask pattern, as illustrated in FIGS. 5–9. Further, the exposed portions of a negative photoresist become substantially less soluble in the development solution. Thus, the exposed portions of a negative photoresist layer remain after development.

Positive-tone materials (e.g., positive tone polyimides) may also be employed with aspects of the present invention. With a positive tone material (sometimes referred to as a positive photoresist or a soluble photoresist), the patterns formed during exposure and development are "images" of the mask pattern. Because positive photoresists are soluble in a developing solution after having been exposed to the radiation source (e.g., a UV or DUV source), the exposed portions are removed during development.

Further, if a positive tone photoimageable layer is used, overexposing a girder layer simply results in overexposing open areas, without serious adverse consequences in the structure (unless the overexposure is severe). But overexposing columns can result in exposing away material from a prior layer that was intended to be protected. Accordingly, it should be understood that, with the benefit of the present disclosure, the processes disclosed and described herein in the context of negative photoresists may be adapted for use with positive photoresist materials.

Also, while the foregoing descriptions involve a scenario using only one mask with each layer/exposure, multiple masks per layer/exposure may be used for various reasons. For instance, a layer of photoimageable material may be spun on (e.g., at 5 microns thick) and exposed through a first mask to create columns/posts. Thereafter, the first mask can be replaced with a second mask corresponding to a girder pattern (connecting the posts). If the material is exposed through the second "girder" mask with a reduced dosage (in terms of energy and/or time of exposure), as compared to the first exposure of that material, a single layer can be formed that includes both girder regions and post regions. For some embodiments of lattice structures, this approach is preferred.

FIG. 6 illustrates a top view of post layer 56, including the material that has been cross-linked as a result of the UV (or DUV) exposure.

It should be understood that additional, known process steps will often be useful. For example, it is known in the art to apply a thin layer of an adhesion promoter to the substrate to help polyimide stick during spin coating.

Figure 10B:
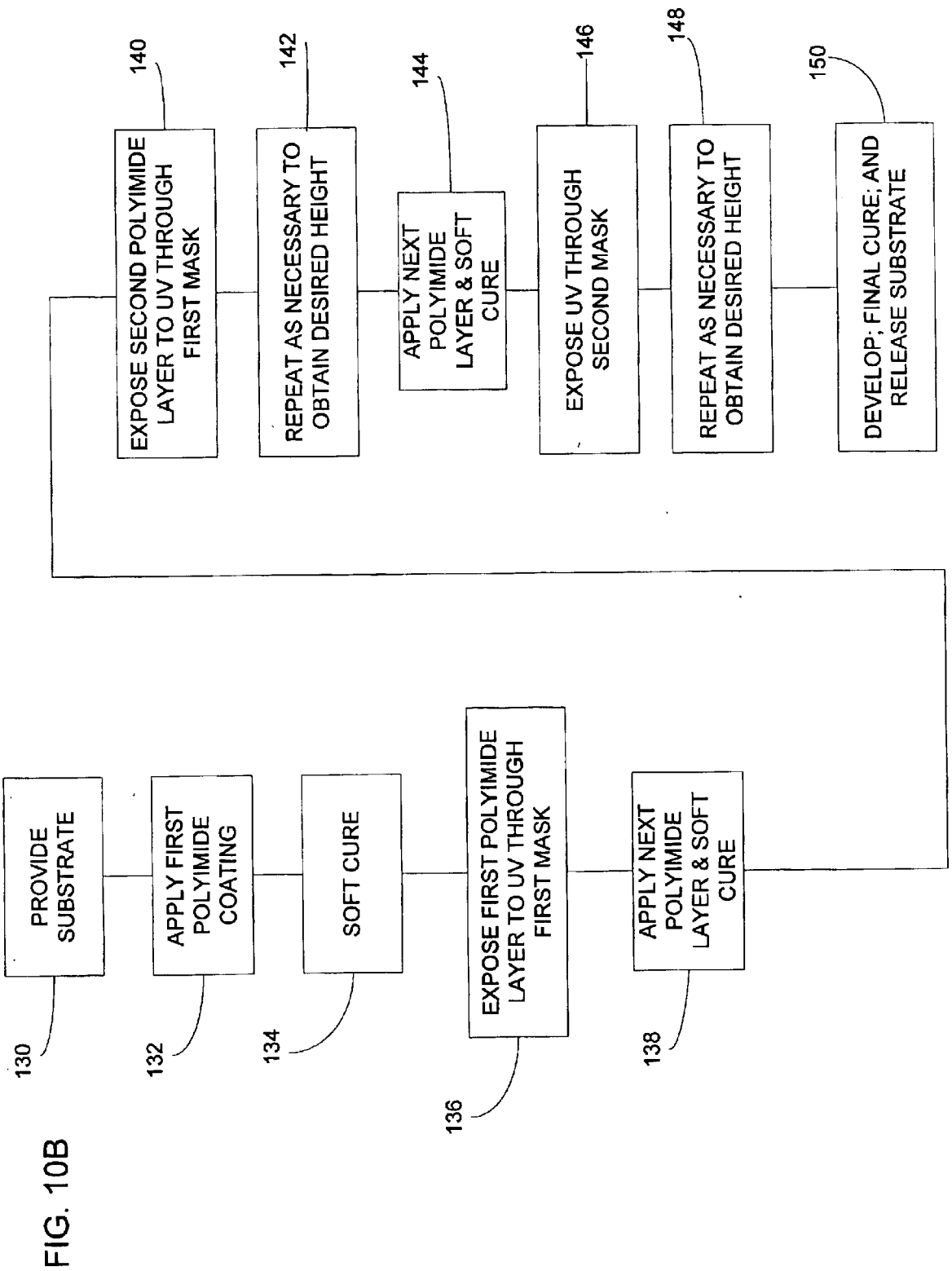
FIG. 10B is a flow chart illustrating pertinent steps of another exemplary method of fabricating three dimensional structures, in accordance with aspects of the present invention, including using a common mask for preparing multiple layers.

FIGS. 10A–10C are flow charts illustrating pertinent steps associated with exemplary methods of fabricating three dimensional structures in accordance with aspects of the invention. FIG. 10A illustrates a method suitable for fabricating a three dimensional structures in accordance with the process illustrated in FIGS. 5–9. A suitable substrate layer 60 (e.g., a silicon wafer) is provided at block 102. At block 104, a first coating of a biocompatible photoimageable material 62, such as polyimide, is applied to substrate layer 60. A first mask is prepared that has a pattern corresponding to a first layer (e.g., post layer 56) of the porous three dimensional structure to be fabricated (block 106). At block 108, the first coating is exposed to UV (or DUV) energy through the first mask to cause the exposed portions of photoimageable material 62 to cross link. Thereafter, at blocks 110–114, the process generally repeats for the second layer (e.g., girder layer 52) and any subsequent layers of the three dimensional structure to be fabricated. At block 118, any remaining unexposed regions of polyimide are developed and removed. Optionally, ultrasonic agitation is used to assist the development process. At block 120, the fabricated structure is cured and released from substrate layer 60. When DUV energy is used, the method may be referred to as a DUV lithographic process.

It should be understood that additional processing steps may be employed if desired. For example, a soft cure (sometimes referred to as a partial cure or a soft bake) may be applied between each layer or some select layers. This is depicted in FIG. 10A block 111 (shown in phantom). Such a soft cure, performed on photoimageable materials prior to exposure, helps to drive off excess solvents and tends to decrease the likelihood of the material shifting on the wafer surface prior to exposure. A material shift can cause non-uniformities in layer thickness, degrading the results of the lithographic process. Soft curing can also help the layers form together properly, thereby improving the integrity of the final structure. Although FIG. 10 illustrates a soft cure occurring only once, as part of the second layer processing, soft curing can be employed for each layer as well.

When desired, a soft bake of about 1 minute at about 70–110 degrees C. (e.g., 100 degrees C.) may be performed on a hot plate or similar device. The actual temperature and duration will vary, depending upon, for example, the material used and the thickness of the coating. A final hard bake (final cure) is performed around 350 degree C., for an hour or more (e.g., two hours). An oven available under the name BLUE M is suitable for such a hard bake. The temperature of the final hard bake is chosen to be higher than the polyimide glass transition temperature and will pull the layers together into a monolithic sample. For example, processing two separately applied layers of polyimide together in such a final bake makes it impracticable to distinguish the interface between the two layers. As mentioned above, the hotplate and polyimide application (i.e., spinning and so on) can be accomplished on a multi-step system, such as the MTI TARGETRACK system, available from Machine Technology, Inc., of Parsippany, N.J.

As stated above, each layer after the first is produced by repeating generally similar steps. In other words, after a layer is completed, and if another layer is desired, another coating of photoimageable material is applied (i.e., at a desired rib thickness corresponding to the height/thickness of the layer to be produced), another mask is prepared and positioned between the exposure source and the photoimageable material, and portions of the photoimageable material are cross-linked by UV (or DUV, depending on the material used) energy exposure through the mask. The process of adding photoimageable material to prepare additional structural layers is sometimes referred to as lamination. If a subsequent layer differs from the preceding layer, a different mask is used. For example, a mask for use in preparing a girder layer would have a form corresponding to the view of a girder layer such as that depicted in FIG. 8.

When a subsequent layer of the porous three dimensional structure is to be substantially identical to one or more prior layers, it is preferable to use the same mask for each of the similar layers. In some applications, however, differences in layers are desired. For example, the present method may be used to produce structures having more complex shapes, as compared with the exemplary structures of FIGS. 1–4. One way to accommodate such differences is to provide unique masks for each unique layer to achieve desired differences in geometric characteristics between such layers. Another way, however, is to de-focus the exposure source (e.g., UV source 70). By de-focusing, the resultant layer will have different geometric characteristics from "related" layers even though the same mask has been used, thereby allowing a smaller set of masks to be used.

Upon completion of lamination and exposure of a desired number of layers, the entire structure is preferably developed to remove substantially all of the biocompatible photoimageable material (e.g., polyimide) that has not been cross-linked by exposure to UV energy (or DUV energy). In general, development involves exposing the structure to a solvent-based solution. The exact development process and type of solvent used generally depends on the photoimageable material used. Such considerations are discussed above in connection with exemplary photoimageable materials suitable for use in connection with aspects of the present invention. In one embodiment, ultrasonic agitation assists in the development of far reaching corners of the structure. After removing the remaining biocompatible photoimageable material, the structure is preferably cured and lifted off of substrate layer 60 by etching a thin oxide on the surface of the sample. The result of the process described herein is a three dimensional lattice structure produced without processing subsequent layers over severe topography, as is required by prior art methods. Other advantages include precise control over layer thickness (which translates into control over the thickness of the layers of the final structure), micron and sub-micron resolution of virtually any three-dimensional structure, and relatively few process tools.

FIG. 10B illustrates pertinent steps of another exemplary method of fabricating three dimensional structures. FIG. 10B is similar to FIG. 10A in several respects. In general, FIG. 10B is intended to highlight that, for some structures and/or layers (e.g., tall post layers), multiple iterations of material application and exposure may be needed. This is shown in FIG. 10B by blocks 132–142, and blocks 144–148. For example, a tall post layer may require several applications of photoimageable material, exposing each application of material through the same mask, in order to create a post layer having the desired height.

One reason why multiple iterations may be useful in some cases is that typical photoimageable materials yield aspect ratios of about 2:1 or so. For example, a one micron diameter post is well defined at a height (layer thickness) of about 2 microns. The inventive processes disclosed herein, however, permit resolutions in excess of 2:1 by using a layer-by-layer approach. Thus, for example, with the present invention a post about 8 microns tall and having about a 1 micron diameter can be achieved. For such a post, the process illustrated in FIG. 10B could be used to spincoat/expose four coatings of polyimide, each about 2 microns in height, resulting in a layer of 8 micron posts.

Further, the final cure (e.g., block 120 of FIG. 10A and block 150 of FIG. 10B) can lead to shrinkage in layer thicknesses. If more precise layer dimensions are important to a given application, the application layers of photoimageable material may be applied at thicker levels to account for shrinkage.

FIG. 10C illustrates pertinent steps of another exemplary method of fabricating three dimensional structures. FIG. 10B is similar to FIGS. 10A and 10B in several respects. FIG. 10C illustrates using a plurality of masks in connection with a first coating of photoimageable material. This is illustrated, for example, at blocks 166–170.

Another advantage of the present methods of manufacturing porous three dimensional structures for implantation into a host, over prior art methods, is that the present method allows each new layer to become cross-linked with the prior layer. This permits greater control of the alignment of each layer, can improve the structural integrity of the final structure, and thereby ensure greater biocompatibility with the host. Alignment marks are useful to improve the alignment of between layers of the porous three dimensional structures. There are standards available from the integrated circuit industry such as, for example, the dark field alignment system (DFAS). DFAS involves a set of reticles, and plus and minus marks that are embedded into the lithography on the outskirts of the wafer being processed (e.g., substrate 60) to provide alignment reference points.

Prior art techniques, such as many current micro electro-mechanical systems (MEMS) techniques, traditionally produce three dimensional parts that are basically extruded two dimensional patterns. In comparison, the aspects of the present invention directed to layered manufacturing allows for a simplified process, providing for more layers and increased three-dimensional flexibility. In comparison with prior art rapid prototyping processes, the present layered manufacturing processes allow for much finer resolution. For example, rapid prototyping techniques provide resolution in the 10–100 micron range. The layered processes disclosed herein provide micron-scale resolution. For example, with presently available materials and equipment, layer thicknesses and lateral lithographic definitions can be achieved down to about 0.5 microns. Also, greater resolutions will be possible with advances in materials and/or equipment.

Another advantage of aspects of the method of the present invention, is that the method lends itself to being combined with other microfabricated devices. For example, a porous three dimensional structure may be manufactured in connection with implant devices such as sensors, micropumps, microchip medication delivery devices and so on. Thus, the present method may be adapted to form biocompatible surfaces/layers on implant devices to improve a biocompatibility of such implant devices when implanted in a host by prompting vascularization adjacent to the device. In one form, a latticework three dimensional structure is prepared (such as a structure similar to those illustrated in FIGS. 1, 4) and thereafter applied to the implant device. Simple applications include bonding the two structures (i.e., the implant device and the latticework) together. More complicated applications include integrating the bottom layer of the two structures (e.g., fabricating the latticework directly on the same substrate/wafer upon which the implant device is fabricated), or having the latticework wrap around the potential implant during or after manufacture.

Figure 11A:
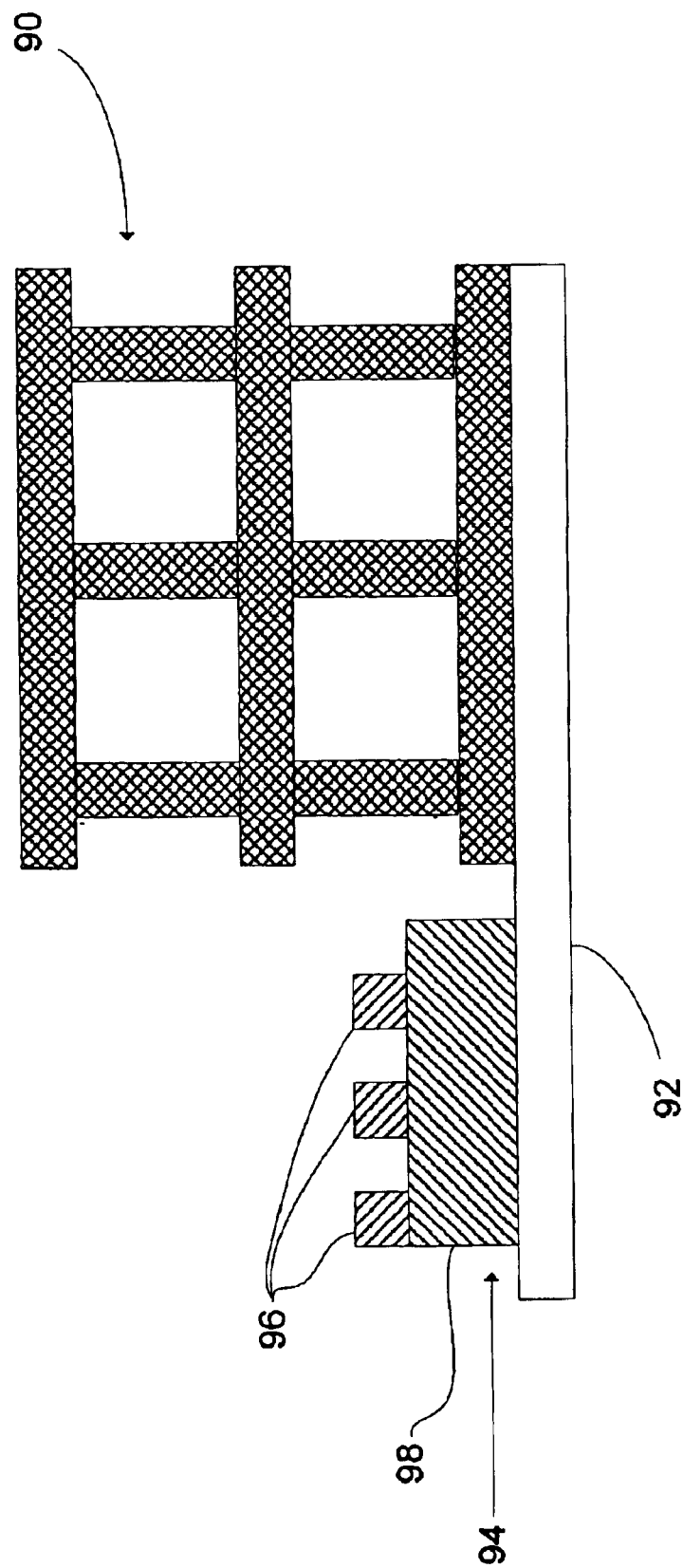
FIG. 11A is a schematic representation of a porous three dimensional latticework fabricated on a substrate in common with an implant device, in accordance with aspects of the present invention.

FIG. 11A is a schematic representation of a porous three dimensional latticework (indicated generally by reference 90) fabricated on a substrate 92 in common with an implant device (indicated generally by reference 94). In one embodiment, the dimensional aspects of the latticework 90 are selected in accordance with the disclosure of the Pekkarinen et al. application to promote vascularization in an area adjacent the implant device 94 when suitably implanted in a host. As mentioned above, implant device 94 may comprise one or more microstructures suitable for implantation in a host, such structures include microsensors, micropumps, microchip medication delivery devices, and/or communication electronics, and the like. In the illustrated embodiment, implant device 94 schematically represents an implantable fluid delivery structure having fluid cells 96 that are constructed and arranged to release a fluid (e.g., a medication) in response to a control input from a controller 98. It should be appreciated that, with the benefit of applicant's invention, the type and number of such implant devices that may be used in connection with the porous three dimensional structure are varied and vast.

Figure 11B:
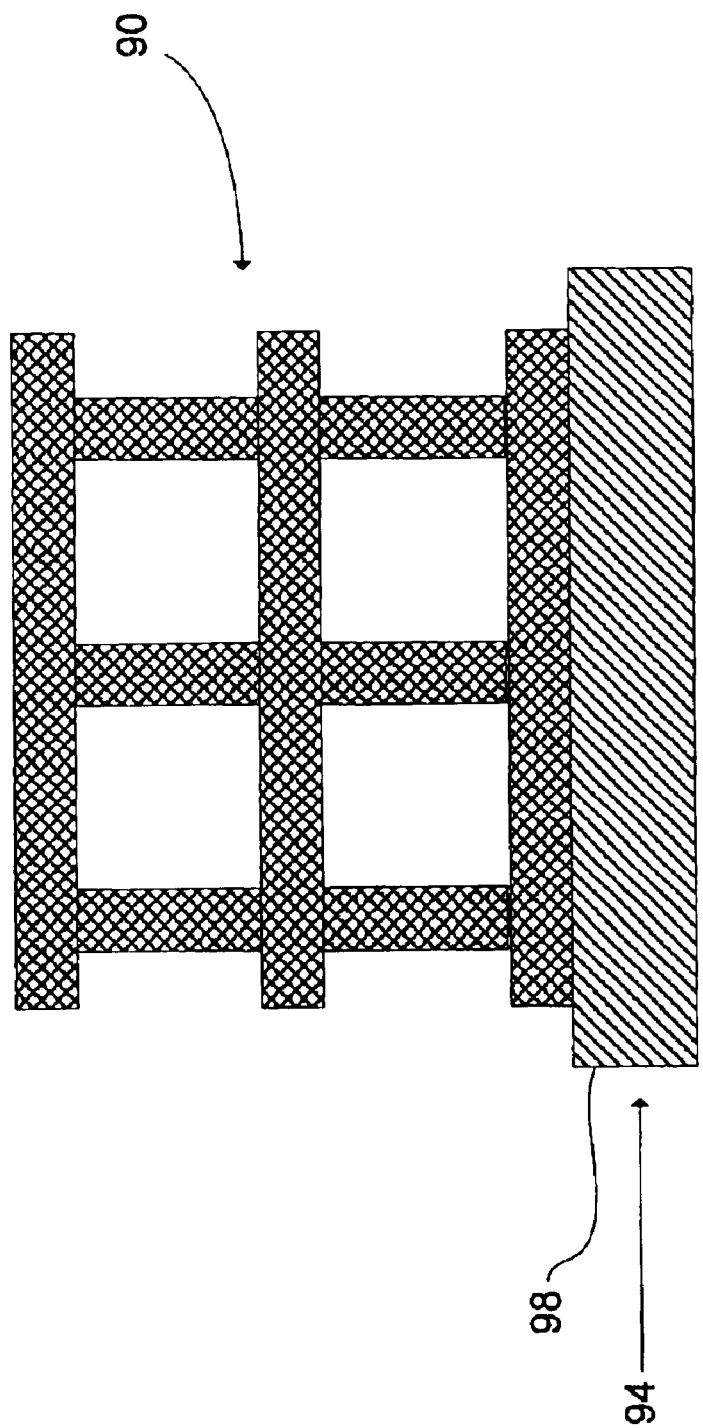
FIG. 11B is a schematic representation of a porous three dimensional latticework fabricated on top of an implant device, in accordance with aspects of the present invention.

FIG. 11B is a schematic representation of a porous three dimensional latticework fabricated on top of the implant device 94. In the illustrated embodiment, the implant device is previously fabricated and comprises a substrate on which the latticework fabricated. Such a structure requires no separate lift off in final form.

It is to be understood the methods of manufacturing disclosed and described herein may be extended to the manufacture of additional structures. FIGS. 12 and 13 illustrate, in schematic form, one possible structure manufactured according to aspects of the present invention. More specifically, FIG. 12 is a schematic representation of a three dimensional structure corresponding to a conical nozzle 200, in accordance with aspects of the present invention. FIG. 13 is an exploded view of the nozzle schematically depicted in FIG. 12.

The nozzle 200 comprises a series of layers 202 which may have uniform or varying thicknesses. Each layer is prepared in a layer by layer manner substantially similar to that described above with respect to FIGS. 5–10. For example, a first layer 204 is prepared using a mask having an annular pattern and applying a photoimageable material at a thickness corresponding to the desired thickness of the first layer 204. Subsequent layers are prepared similarly, resulting in nozzle structure 200. In the illustrated embodiment, for example, each layer is produced by spin coating and exposing a series of annular patterns having substantially constant outer diameters but generally decreasing inner diameters. The result is a structure having a generally cylindrical outer shape and having a generally conically shaped opening therethrough.

In constructing a structure, such as conical nozzle 200, different lithographic masks may be used for each layer. Alternatively, the exposure source (e.g., UV or DUV light) may be focused/defocused to achieve slightly larger/smaller inner diameters of the conical shape. With such a defocusing approach, it is possible to prepare several layers (e.g., three) per mask. In this regard, the defocus would be with respect to the distance held between the exposure source and the mask.

Another advantage of the layered manufacturing techniques of the present invention is that each layer thickness can be unique, with desired adjustments in the photoimageable material application and exposure dosage. For example, different grades of photoimageable polyimide and/or different spin speeds can be used to create different thicknesses for each layer, as desired.

With the foregoing description in mind, it should now be appreciated that the layered manufacturing techniques described herein can be used to create three dimensional structures having many, many layers. When exposure proceeds on a layer by layer basis, while development occurs later, each subsequent layer is spin-coated (or otherwise laminated) onto a previous layer that is substantially flat. In contrast, prior art techniques require processing over non-flat topography created by prior processing steps (e.g., developing). Such processing over topography renders lithographic manufacturing processes very difficult and impracticable because spin coating (or otherwise laminating) over topographic structures results in much less uniform layer thicknesses. This lack of uniformity causes problems with focusing, exposure, and development. Further, when layer thickness is important (e.g., when fabricating porous structures intended to promote vascularization when implanted in a host), non-uniformity of thickness may render the structure unusable. Thus, the manufacturing techniques disclosed herein provide distinct advantages, unknown in the prior art, leading to a very high number of layers that can be produced, and providing better vascularization.

Finally, although the foregoing descriptions and accompanying figures are generally directed to fabricating individual pieces and small pieces intended for implantation, the methods disclosed herein are scalable. For example, the disclosed processes can be used to fabricate wafer-sized, three dimensional structures. Likewise, a plurality of structures can be fabricated in a single batch.

In view of the above, it will be seen that the several objects of the invention are achieved and other advantageous results attained.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A method of manufacturing a three dimensional structure having at least a first layer and a second layer, said method comprising:
   providing a substrate layer;
   applying a first coating of a photoimageable material to the substrate layer;
   preparing a first mask having a pattern corresponding to the first layer of the three dimensional structure to be manufactured;
   exposing the first coating of the photoimageable material with an exposure source through the first mask such that the first layer of the three dimensional structure is provided;
   applying a second coating of the photoimageable material subsequent to the first layer of the three dimensional structure;
   preparing a second mask having a pattern corresponding to the second layer of the three dimensional structure to be manufactured;
   exposing the second coating of the photoimageable material with the exposure source through the second mask such that the second layer of the three dimensional structure is provided; and
   developing and removing regions of said first and second coatings that do not correspond to a layer of the three dimensional structure.

2. A method of manufacturing a three dimensional structure as set forth in claim 1 wherein:
   exposing the first coating of the photoimageable material with the exposure source through the first mask cross-links exposed areas of said first coating;
   exposing the second coating of the photoimageable material with the exposure source through the second mask cross-links exposed areas of said second coating; and
   developing and removing regions of said first and second coatings removes unexposed areas of said first and second coatings.

3. A method of manufacturing a three dimensional structure as set forth in claim 2 wherein the three dimensional structure comprises a porous three dimensional structure for implantation in a host capable of producing an inflammatory foreign body response, wherein at least one of the first and second layers has a plurality of openings sized to permit fluid and inflammatory cells of the host to pass through the openings and migrate into an interior volume of the porous three dimensional structure and sized to promote a non-flattened morphology of the inflammatory cells, and the porous three dimensional structure promoting vascularization adjacent said structure when implanted into the host, and wherein the first coating of the photoimageable material comprises a biocompatible photoimageable material such that applying the first coating of the photoimageable material to the substrate layer comprises applying the biocompatible photoimageable material to the substrate layer and applying the second coating of the photoimageable material to the first layer comprises applying the biocompatible photoimageable material to the first layer.

4. A method of manufacturing a three dimensional structure as set forth in claim 3 wherein the biocompatible photoimageable material comprises a polyimide and the exposure source comprises a UV energy source.

5. A method of manufacturing a three dimensional structure as set forth in claim 3 wherein the biocompatible photoimageable material comprises a polyimide and the exposure source comprises a DUV energy source.

6. A method of manufacturing a three dimensional structure as set forth in claim 3 wherein one of the first and second layers has a cross section corresponding to a layer of girder sections and the other one of the first and second layers has a cross section corresponding to a layer of post sections.

7. A method of manufacturing a three dimensional structure as set forth in claim 3 further comprising:
   applying a third coating of the biocompatible photoimageable material subsequent to the second layer of the porous three dimensional structure;
   preparing a third mask having a pattern corresponding to a third layer of the porous three dimensional structure to be manufactured; and
   exposing the third coating of the biocompatible photoimageable material with the exposure source through the third mask whereby the exposed areas of said third coating become cross-linked such that the third layer of the porous three dimensional structure is provided and the first, second and third layers are cross-linked.

8. A method of manufacturing a three dimensional structure as set forth in claim 7 wherein the third mask is substantially identical to the first mask and wherein the third layer has a cross section substantially identical to a cross section of the first layer.

9. A method of manufacturing a three dimensional structure as set forth in claim 7 wherein preparing the third mask comprises using the first mask.

10. A method of manufacturing a three dimensional structure as set forth in claim 9 wherein exposing the third coating of the biocompatible photoimageable material with the exposure source through the third mask comprises defocusing the exposure of the third coating of the biocompatible photoimageable material through the first mask such that the third layer has a different geometric characteristic from the first layer.

11. A method of manufacturing a three dimensional structure as set forth in claim 7 further comprising:
    applying a fourth coating of the biocompatible photoimageable material subsequent to the third layer of the porous three dimensional structure;
    preparing a fourth mask having a pattern corresponding to a fourth layer of the porous three dimensional structure to be manufactured; and
    exposing the fourth coating of the biocompatible photoimageable material with the exposure source through the fourth mask whereby the exposed areas of said fourth coating become cross-linked such that a fourth layer of the porous three dimensional structure is provided and the first, second, third, and fourth layers are cross-linked.

12. A method of manufacturing a three dimensional structure as set forth in claim 11 wherein the fourth mask is substantially identical to the second mask and wherein the fourth layer has a cross section substantially identical to a cross section of the second layer.

13. A method of manufacturing a three dimensional structure as set forth in claim 11 wherein preparing the fourth mask comprises using the second mask.

14. A method of manufacturing a three dimensional structure as set forth in claim 13 wherein exposing the fourth coating of the biocompatible photoimageable material with the exposure source through the fourth mask comprises defocusing the exposure of the fourth coating of the biocompatible photoimageable material through the second mask such that the fourth layer has a different geometric characteristic from the second layer.

15. A method of manufacturing a three dimensional structure as set forth in claim 3 wherein the substrate layer is a glass, a quartz, or a plastic layer.

16. A method of manufacturing a three dimensional structure as set forth in claim 3 wherein the substrate layer comprises a silicon wafer.

17. A method of manufacturing a three dimensional structure as set forth in claim 16 wherein the biocompatible photoimageable material comprises a polyimide and wherein applying the first coating of the biocompatible photoimageable material to the substrate layer comprises spincoating the polyimide on to the silicon wafer at a rib thickness.

18. A method of manufacturing a three dimensional structure as set forth in claim 3 wherein:
   applying the first coating of the biocompatible photoimageable material comprises applying polyimide at a first thickness corresponding to a desired post length such that the first layer of the porous three dimensional structure corresponds to one or more posts having the desired post length;
   applying the second coating of the biocompatible photoimageable material comprises applying polyimide at a second thickness corresponding to a desired girder thickness such that the second layer of the porous three dimensional structure corresponds to one or more girders having the desired girder thickness; and
   wherein the first and second layers are cross-linked such that the one or more posts cooperate with the one or more girders to form at least a portion of the porous three dimensional structure.

19. A method of manufacturing a three dimensional structure as set forth in claim 3 wherein:
   applying the first coating of the biocompatible photoimageable material comprises applying polyimide at a first thickness corresponding to a desired girder thickness such that the first layer of the porous three dimensional structure corresponds to one or more girders having the desired girder thickness; and
   applying the second coating of the biocompatible photoimageable material comprises applying polyimide at a second thickness corresponding to a desired post length such that the second layer of the porous three dimensional structure corresponds to one or more posts having the desired post length; and
   wherein the first and second layers are cross-linked such that the one or more posts cooperate with the one or more girders to form at least a portion of the porous three dimensional structure.

20. A method of manufacturing a three dimensional structure as set forth in claim 3 wherein the biocompatible photoimageable material comprises a polyimide and wherein developing unexposed regions of the first and second coatings of the biocompatible photoimageable material comprises applying a developing solution to the porous three dimensional structure to develop and remove unexposed polyimide coating regions.

21. A method of manufacturing a three dimensional structure as set forth in claim 20 further comprising using ultrasonic agitation to assist in developing the unexposed polyimide coating regions.

22. A method of manufacturing a three dimensional structure as set forth in claim 3 further comprising curing the porous three dimensional structure.

23. A method of manufacturing a three dimensional structure as set forth in claim 3 wherein the substrate layer comprises a silicon-based material and the method further comprising releasing the substrate layer by etching a thin oxide layer on the surface of the silicon-based material.

24. A method of manufacturing a three dimensional structure as set forth in claim 3 further comprising providing one or more sacrificial layers between the substrate layer and the first layer.

25. A method of manufacturing a three dimensional structure as set forth in claim 3 further comprising soft curing the first coating before exposing the first coating and soft curing the second coating before exposing the second coating.

26. A method of manufacturing a three dimensional structure as set forth in claim 3 further comprising applying the porous three dimensional structure to a microfabricated sensor.

27. A method of manufacturing a three dimensional structure as set forth in claim 3 further comprising applying the porous three dimensional structure to a micropump.

28. A method of manufacturing a three dimensional structure as set forth in claim 3 further comprising applying the porous three dimensional structure to a microchip medication delivery device.

29. A method of manufacturing a three dimensional structure as set forth in claim 3 further comprising applying the porous three dimensional structure to an electronic communication device.

30. A method of manufacturing a three dimensional structure as set forth in claim 1 wherein the photoimageable material comprises a positive tone polyimide and the exposure source is a UV source or a DUV source.

31. A method of manufacturing a three dimensional structure as set forth in claim 1 wherein the photoimageable material comprises a negative tone polyimide and the exposure source is a UV source or a DUV source.

32. A method of manufacturing a three dimensional structure as set forth in claim 1 wherein the three dimensional structure comprises the first layer, the second layer, and at least another layer, the method further comprising:
   applying another coating of the photoimageable material subsequent to the second layer of the three dimensional structure;
   preparing another mask having a pattern corresponding to the other layer of the three dimensional structure; and
   exposing the other coating of the photoimageable material with the exposure source through another mask to provide the other layer.

33. A method of manufacturing a three dimensional structure as set forth in claim 32 wherein the other mask is a third mask different from the first mask and the second mask.

34. A method of manufacturing a three dimensional structure as set forth in claim 32 wherein the other mask is the first mask or the second mask.

35. A method of manufacturing a three dimensional structure as set forth in claim 32 wherein first layer has a first thickness, the second layer has a second thickness, and the other layer has a third thickness that is substantially the same as the first thickness or the second thickness.

36. A method of manufacturing a three dimensional structure as set forth in claim 32 wherein applying the first coating, the second coating, and the other coating comprises applying said coatings such that each of said coatings is substantially flat at least prior to exposure to the exposure source.

37. A method of manufacturing a three dimensional structure having at least a first layer and a second layer, said method comprising:
   providing a substrate layer;
   applying a first coating of photoimageable material at a position subsequent to the substrate layer;
   preparing a first mask having a pattern corresponding to at least a first portion of the first layer of the three dimensional structure to be manufactured;
   exposing the first coating with an exposure source through the first mask such that at least a first portion of the first layer is formed;
   applying a second coating of photoimageable material subsequent to the first layer;
   preparing a second mask having a pattern corresponding to at least a first portion of the second layer of the three dimensional structure to be manufactured;
   exposing the second coating with the exposure source through the second mask such that at least a first portion of the second layer is formed; and
   applying a developing process to remove regions of the photoimageable material that do not correspond to the first and second layers.

38. A method of manufacturing a three dimensional structure as set forth in claim 37 further comprising:
   preparing a third mask having a pattern corresponding to a second portion of the first layer of the three dimensional structure to be manufactured; and
   exposing the first coating with the exposure source through the third mask prior to applying the second coating, whereby a second portion of the first layer is formed.

39. A method of manufacturing a three dimensional structure as set forth in claim 37 further comprising:
   preparing a third mask having a pattern corresponding to a second portion of the second layer of the three dimensional structure to be manufactured; and
   exposing the second coating with the exposure source through the third mask whereby a second portion of the second layer is formed.

40. A method of manufacturing a three dimensional structure as set forth in claim 37 wherein the three dimensional structure comprises a porous three dimensional structure for implantation in a host capable of producing an inflammatory foreign body response, wherein at least one of the first and second layers has a plurality of openings sized to permit fluid and inflammatory cells of the host to pass through the openings and migrate into an interior volume of the porous thee dimensional structure and sized to promote a non-flattened morphology of the inflammatory cells, and the porous three dimensional structure promoting vascularization adjacent said structure when implanted into the host, and wherein the first coating of the photoimageable material comprises a biocompatible photoimageable material such that applying the first coating of the photoimageable material comprises applying the biocompatible photoimageable material at a position subsequent to the substrate layer and applying the second coating of the photoimageable material subsequent to the first layer comprises applying the biocompatible photoimageable material subsequent to the first layer.

41. A method of manufacturing a three dimensional structure as set forth in claim 37 wherein the photoimageable material comprises a polyimide and the exposure source comprises a UV energy source.

42. A method of manufacturing a three dimensional structure as set forth in claim 37 wherein the photoimageable material comprises a polyimide and the exposure source comprises a DUV energy source.

43. A method of manufacturing a three dimensional structure as set forth in claim 37 wherein one of the first and second layers has a cross section corresponding to a layer of girder sections and the other one of the first and second layers has a cross section corresponding to a layer of post sections whereby the three dimensional structure comprises a latticework structure.

44. A method of manufacturing a three dimensional structure as set forth in claim 37 wherein a first portion of one of the first and second layers corresponds to girder sections and a second portion of one of the first and second layers corresponds to post sections whereby the three dimensional structure comprises a latticework structure.

45. A method of manufacturing a three dimensional structure as set forth in claim 37 wherein providing the substrate layer comprises providing a glass layer, a quartz layer or a plastic layer.

46. A method of manufacturing a three dimensional structure as set forth in claim 37 wherein providing substrate layer comprises providing a silicon wafer.

47. A method of manufacturing a three dimensional structure as set forth in claim 37 wherein the photoimageable material comprises a positive tone material and applying the developing process comprises applying a developing solution for removing photoimageable material exposed with the exposure source such that unexposed photoimageable material substantially remains at the completion of the developing process.

48. A method of manufacturing a three dimensional structure as set forth in claim 37 wherein the photoimageable material comprises a negative tone material and applying the developing process comprises applying a developing solution for removing photoimageable material not exposed with the exposure source such that exposed photoimageable material substantially remains at the completion of the developing process.

49. A method of manufacturing a three dimensional structure as set forth in claim 37 further comprising curing the three dimensional structure.

50. A method of manufacturing a three dimensional structure as set forth in claim 37 further comprising providing one or more sacrificial layers between the substrate layer and the first layer.

51. A method of manufacturing a structure for implantation in a host, said structure including a porous three dimensional structure having at least first and second layers and being sized and shaped for producing an inflammatory foreign body response, wherein at least one of the first and second layers has a plurality of openings sized to permit fluid and inflammatory cells of the host to pass through the openings and migrate into an interior volume of the porous thee dimensional structure and sized to promote a non-flattened morphology of the inflammatory cells, and the porous three dimensional structure promoting vascularization adjacent said structure when implanted into the host, said method comprising:
   providing a microfabricated medical implant device constructed and arranged for implantation in the host, said microfabricated sensor comprising a substrate layer onto which the porous three dimensional structure can be manufactured;
   applying a first coating of photoimageable material to the substrate layer;

preparing a first mask having a pattern corresponding to at least a first portion of the first layer of the three dimensional structure to be manufactured;

exposing the first coating with an exposure source through the first mask such that at least a first portion of the first layer is formed;

applying a second coating of photoimageable material subsequent to the first layer;

preparing a second mask having a pattern corresponding to at least a first portion of the second layer of the three dimensional structure to be manufactured;

exposing the second coating with the exposure source through the second mask such that at least a first portion of the second layer is formed; and applying a developing process to remove regions of the photoimageable material that do not correspond to the first and second layers.

52. A method manufacturing a structure as set forth in claim 51 wherein the medical implant device is a micropump, a microsensor, or a medication delivery device.

* * * * *